US011863878B2

(12) United States Patent
Blanquart et al.

(10) Patent No.: US 11,863,878 B2
(45) Date of Patent: Jan. 2, 2024

(54) YCBCR PULSED ILLUMINATION SCHEME IN A LIGHT DEFICIENT ENVIRONMENT

(71) Applicant: Depuy Synthes Products, Inc., Raynham, MA (US)

(72) Inventors: Laurent Blanquart, Westlake Village, CA (US); John Richardson, Westlake Village, CA (US)

(73) Assignee: Depuy Synthes Products, Inc., Raynham, MA (US)

( * ) Notice: Subject to any disclaimer, the term of this patent is extended or adjusted under 35 U.S.C. 154(b) by 114 days.

(21) Appl. No.: 17/374,907

(22) Filed: Jul. 13, 2021

(65) Prior Publication Data

US 2021/0344885 A1 Nov. 4, 2021

Related U.S. Application Data

(60) Continuation of application No. 16/940,189, filed on Jul. 27, 2020, now Pat. No. 11,070,779, which is a
(Continued)

(51) Int. Cl.
*H04N 23/84* (2023.01)
*A61B 1/045* (2006.01)
(Continued)

(52) U.S. Cl.
CPC ....... *H04N 23/84* (2023.01); *A61B 1/000095* (2022.02); *A61B 1/045* (2013.01);
(Continued)

(58) Field of Classification Search
CPC ........ H04B 10/54; H04B 10/67; H04N 9/045; H04N 5/378; H04N 5/2256; H04N 5/2354;
(Continued)

(56) References Cited

U.S. PATENT DOCUMENTS 3,666,885 A 5/1972 Hemsley et al.
4,011,403 A 3/1977 Epstein et al.
(Continued)

FOREIGN PATENT DOCUMENTS

CN 1520696 A 8/2004
CN 101079966 A 11/2007
(Continued)

OTHER PUBLICATIONS

Blumenfeld, et al. Three dimensional image registration of MR proximal femur images for the analysis of trabecular bone parameters. Oct. 2008. [retrieved on Jul. 30, 2014] Retrieved from the internet: <URL: http://www.ncbi.nlm.nih.gov/pmc/articles/PMC2673590/>.
(Continued)

*Primary Examiner* — Nathnael Aynalem
(74) *Attorney, Agent, or Firm* — TechLaw Ventures, PLLC; Terrence J. Edwards

(57) ABSTRACT

The disclosure extends to methods, systems, and computer program products for producing an image in light deficient environments with luminance and chrominance emitted from a controlled light source.

20 Claims, 19 Drawing Sheets

Related U.S. Application Data continuation of application No. 16/398,114, filed on Apr. 29, 2019, now Pat. No. 10,785,461, which is a continuation of application No. 15/701,264, filed on Sep. 11, 2017, now Pat. No. 10,277,875, which is a continuation of application No. 15/369,170, filed on Dec. 5, 2016, now Pat. No. 9,762,879, which is a division of application No. 13/952,570, filed on Jul. 26, 2013, now Pat. No. 9,516,239.

(60) Provisional application No. 61/790,487, filed on Mar. 15, 2013, provisional application No. 61/791,473, filed on Mar. 15, 2013, provisional application No. 61/790,719, filed on Mar. 15, 2013, provisional application No. 61/676,289, filed on Jul. 26, 2012.

(51) Int. Cl.
| | | |
|---|---|---|
| *A61B 1/06* | (2006.01) | |
| *A61B 1/05* | (2006.01) | |
| *A61B 1/00* | (2006.01) | |
| *H04N 23/10* | (2023.01) | |
| *H04N 23/12* | (2023.01) | |
| *H04N 23/56* | (2023.01) | |
| *H04N 23/74* | (2023.01) | |
| *H04N 25/11* | (2023.01) | |
| *H04N 25/70* | (2023.01) | |
| *H04N 25/75* | (2023.01) | |
| *H04N 1/60* | (2006.01) | |
| *H04N 5/04* | (2006.01) | |
| *H04N 9/64* | (2023.01) | |
| *H04N 9/77* | (2006.01) | |
| *H04N 23/50* | (2023.01) | |
| *H04N 25/76* | (2023.01) | |
| *H04N 9/07* | (2006.01) | |

(52) U.S. Cl.
CPC ............. *A61B 1/051* (2013.01); *A61B 1/063* (2013.01); *A61B 1/0638* (2013.01); *A61B 1/0655* (2022.02); *H04N 1/6016* (2013.01); *H04N 5/04* (2013.01); *H04N 9/07* (2013.01); *H04N 9/646* (2013.01); *H04N 23/10* (2023.01); *H04N 23/12* (2023.01); *H04N 23/56* (2023.01); *H04N 23/74* (2023.01); *H04N 25/11* (2023.01); *H04N 25/70* (2023.01); *H04N 25/75* (2023.01); *F04C 2270/041* (2013.01); *H04N 23/555* (2023.01); *H04N 25/76* (2023.01)

(58) Field of Classification Search
CPC .................. H04N 9/07; H04N 1/6016; H04N 2005/2255; H04N 5/04; H04N 5/2355; H04N 5/374; H04N 9/77; H04N 5/35536; H04N 5/355; H04N 5/35581; H04N 5/2353; H04N 5/35563; A61B 1/00009; A61B 1/063; A61B 1/0638; A61B 1/06; G06T 2207/10016; G06T 2207/20208; G06K 9/2027; G06K 9/4652
USPC .................................................. 348/68, 234
See application file for complete search history.

(56) References Cited

U.S. PATENT DOCUMENTS

| | | |
|---|---|---|
| 4,356,534 A | 10/1982 | Hattori |
| 4,363,963 A | 12/1982 | Ando |
| 4,433,675 A | 2/1984 | Konoshima |
| 4,436,095 A | 3/1984 | Kruger |
| 4,473,839 A | 9/1984 | Noda |
| 4,644,403 A | 2/1987 | Sakai et al. |
| 4,651,226 A | 3/1987 | Motoori et al. |
| 4,692,606 A | 9/1987 | Sakai et al. |
| 4,740,837 A | 4/1988 | Yanagisawa et al. |
| 4,741,327 A | 5/1988 | Yabe |
| 4,742,388 A | 5/1988 | Cooper et al. |
| 4,745,471 A | 5/1988 | Takamura et al. |
| 4,773,396 A | 9/1988 | Okazaki |
| 4,782,386 A | 11/1988 | Ams et al. |
| 4,786,965 A | 11/1988 | Yabe |
| 4,832,003 A | 5/1989 | Yabe |
| 4,845,555 A | 7/1989 | Yabe et al. |
| 4,853,772 A | 8/1989 | Kikuchi |
| 4,853,773 A | 8/1989 | Hibino et al. |
| 4,865,018 A | 9/1989 | Kanno et al. |
| 4,866,526 A | 9/1989 | Ams et al. |
| 4,884,133 A | 11/1989 | Kanno et al. |
| 4,884,134 A | 11/1989 | Tsuji et al. |
| 4,908,701 A | 3/1990 | Udagawa |
| 4,918,521 A | 4/1990 | Yabe et al. |
| 4,924,856 A | 5/1990 | Noguchi |
| 4,938,205 A | 7/1990 | Nudelman |
| 4,942,473 A | 7/1990 | Zeevi et al. |
| 4,947,246 A | 8/1990 | Kikuchi |
| 4,953,539 A | 9/1990 | Nakamura et al. |
| 4,959,710 A | 9/1990 | Uehara et al. |
| 4,963,960 A | 10/1990 | Takami |
| 5,001,556 A | 3/1991 | Nakamura et al. |
| 5,016,975 A | 5/1991 | Sasaki et al. |
| 5,021,888 A | 6/1991 | Kondou et al. |
| 5,047,846 A | 9/1991 | Uchiyama et al. |
| RE33,854 E | 3/1992 | Adair |
| 5,103,497 A | 4/1992 | Hicks |
| 5,111,804 A | 5/1992 | Funakoshi |
| 5,133,035 A | 7/1992 | Hicks |
| 5,187,572 A | 2/1993 | Nakamura et al. |
| 5,188,094 A | 2/1993 | Adair |
| 5,196,938 A | 3/1993 | Blessinger |
| 5,200,838 A | 4/1993 | Nudelman et al. |
| 5,220,198 A | 6/1993 | Tsuji |
| 5,228,430 A | 7/1993 | Sakamoto |
| 5,233,416 A | 8/1993 | Inoue |
| 5,241,170 A | 8/1993 | Field, Jr. et al. |
| 5,255,087 A | 10/1993 | Nakamura et al. |
| 5,264,925 A | 11/1993 | Shipp et al. |
| 5,313,306 A | 5/1994 | Kuban et al. |
| 5,325,847 A | 7/1994 | Matsuno |
| 5,365,268 A | 11/1994 | Minami |
| 5,402,768 A | 4/1995 | Adair |
| 5,408,268 A | 4/1995 | Shipp |
| 5,411,020 A | 5/1995 | Ito |
| 5,427,087 A | 6/1995 | Ito et al. |
| 5,454,366 A | 10/1995 | Ito et al. |
| 5,494,483 A | 2/1996 | Adair |
| 5,523,786 A | 6/1996 | Parulski |
| 5,550,595 A | 8/1996 | Hannah |
| 5,558,841 A | 9/1996 | Nakagawa et al. |
| 5,594,497 A | 1/1997 | Ahern et al. |
| 5,627,584 A | 5/1997 | Nishikori et al. |
| 5,658,238 A | 8/1997 | Suzuki et al. |
| 5,665,959 A | 9/1997 | Fossum et al. |
| 5,704,836 A | 1/1998 | Norton et al. |
| 5,730,702 A | 3/1998 | Tanaka et al. |
| 5,734,418 A | 3/1998 | Danna |
| 5,748,234 A | 5/1998 | Lippincott |
| 5,749,830 A | 5/1998 | Kaneko et al. |
| 5,754,313 A | 5/1998 | Pelchy et al. |
| 5,783,909 A | 7/1998 | Hochstein |
| 5,784,099 A | 7/1998 | Lippincott |
| 5,857,963 A | 1/1999 | Pelchy et al. |
| 5,887,049 A | 3/1999 | Fossum |
| 5,924,978 A | 7/1999 | Koeda et al. |
| 5,929,901 A | 7/1999 | Adair et al. |
| 5,949,483 A | 9/1999 | Fossum et al. |
| 5,957,834 A | 9/1999 | Mochida |
| 5,986,693 A | 11/1999 | Adair et al. |
| 5,995,136 A | 11/1999 | Hattori et al. |
| 6,023,315 A | 2/2000 | Harrold et al. |
| 6,038,067 A | 3/2000 | George |

(56) References Cited

U.S. PATENT DOCUMENTS

| | | | |
|---|---|---|---|
| 6,043,839 A | 3/2000 | Adair et al. | |
| 6,139,489 A | 10/2000 | Wampler et al. | |
| 6,141,505 A | 10/2000 | Miyata et al. | |
| 6,142,930 A | 11/2000 | Ito et al. | |
| 6,166,768 A | 12/2000 | Fossum et al. | |
| 6,184,922 B1 | 2/2001 | Saito et al. | |
| 6,184,940 B1 | 2/2001 | Sano | |
| 6,215,517 B1 | 3/2001 | Takahashi et al. | |
| 6,222,175 B1 | 4/2001 | Krymski | |
| 6,239,456 B1 | 5/2001 | Berezin et al. | |
| 6,272,269 B1 | 8/2001 | Naum | |
| 6,275,255 B1 | 8/2001 | Adair et al. | |
| 6,292,220 B1 | 9/2001 | Ogawa et al. | |
| 6,294,775 B1 | 9/2001 | Seibel et al. | |
| 6,310,642 B1 | 10/2001 | Adair et al. | |
| 6,320,331 B1 | 11/2001 | Iida et al. | |
| 6,331,156 B1 | 12/2001 | Haefele et al. | |
| 6,389,205 B1 | 5/2002 | Muckner et al. | |
| 6,416,463 B1 | 7/2002 | Tsuzuki et al. | |
| 6,429,953 B1 | 8/2002 | Feng | |
| 6,444,970 B1 | 9/2002 | Barbato | |
| 6,445,022 B1 | 9/2002 | Barna et al. | |
| 6,445,139 B1 | 9/2002 | Marshall et al. | |
| 6,464,633 B1 * | 10/2002 | Hosoda | A61B 1/0638 348/69 |
| 6,466,618 B1 | 10/2002 | Messing et al. | |
| 6,485,414 B1 | 11/2002 | Neuberger | |
| 6,512,280 B2 | 1/2003 | Chen et al. | |
| 6,567,115 B1 | 5/2003 | Miyashita et al. | |
| 6,627,474 B2 | 9/2003 | Barna et al. | |
| 6,631,230 B1 | 10/2003 | Campbell | |
| 6,659,940 B2 | 12/2003 | Adler | |
| 6,665,013 B1 | 12/2003 | Fossum et al. | |
| 6,677,992 B1 | 1/2004 | Matsumoto et al. | |
| 6,687,534 B2 | 2/2004 | Tsujita | |
| 6,690,466 B2 | 2/2004 | Miller et al. | |
| 6,692,431 B2 | 2/2004 | Kazakevich | |
| 6,707,499 B1 | 3/2004 | Kung et al. | |
| 6,772,181 B1 | 8/2004 | Fu et al. | |
| 6,773,392 B2 | 8/2004 | Kikuchi et al. | |
| 6,791,739 B2 | 9/2004 | Ramanujan et al. | |
| 6,796,939 B1 | 9/2004 | Hirata et al. | |
| 6,799,065 B1 | 9/2004 | Niemeyer | |
| 6,809,358 B2 | 10/2004 | Hsieh et al. | |
| 6,836,288 B1 | 12/2004 | Lewis | |
| 6,838,653 B2 | 1/2005 | Campbell et al. | |
| 6,841,947 B2 | 1/2005 | Berg-johansen | |
| 6,847,399 B1 | 1/2005 | Ang | |
| 6,856,712 B2 | 2/2005 | Fauver et al. | |
| 6,873,363 B1 | 3/2005 | Barna et al. | |
| 6,879,340 B1 | 4/2005 | Chevallier | |
| 6,899,675 B2 | 5/2005 | Cline et al. | |
| 6,900,829 B1 | 5/2005 | Orzawa et al. | |
| 6,906,745 B1 | 6/2005 | Fossum et al. | |
| 6,921,920 B2 | 7/2005 | Kazakevich | |
| 6,933,974 B2 | 8/2005 | Lee | |
| 6,947,090 B2 | 9/2005 | Komoro et al. | |
| 6,961,461 B2 | 11/2005 | MacKinnon et al. | |
| 6,970,195 B1 | 11/2005 | Bidermann et al. | |
| 6,977,733 B2 | 12/2005 | Denk et al. | |
| 6,982,740 B2 | 1/2006 | Adair et al. | |
| 6,998,594 B2 | 2/2006 | Gaines et al. | |
| 6,999,118 B2 | 2/2006 | Suzuki | |
| 7,009,634 B2 | 3/2006 | Iddan et al. | |
| 7,009,648 B2 | 3/2006 | Lauxtermann et al. | |
| 7,030,904 B2 | 4/2006 | Adair et al. | |
| 7,037,259 B2 | 5/2006 | Hakamata et al. | |
| 7,068,878 B2 | 6/2006 | Crossman-Bosworth et al. | |
| 7,071,979 B1 | 7/2006 | Ohtani et al. | |
| 7,079,178 B2 | 7/2006 | Hynecek | |
| 7,102,682 B2 | 9/2006 | Baer | |
| 7,105,371 B2 | 9/2006 | Fossum et al. | |
| 7,106,377 B2 | 9/2006 | Bean et al. | |
| 7,119,839 B1 | 10/2006 | Mansoorian | |
| 7,151,568 B2 | 12/2006 | Kawachi et al. | |
| 7,159,782 B2 | 1/2007 | Johnston et al. | |
| 7,184,084 B2 | 2/2007 | Glenn | |
| 7,189,226 B2 | 3/2007 | Auld et al. | |
| 7,189,961 B2 | 3/2007 | Johnston et al. | |
| 7,194,129 B1 * | 3/2007 | Reinhart | H04N 1/646 382/167 |
| 7,208,983 B2 | 4/2007 | Imaizumi et al. | |
| 7,252,236 B2 | 8/2007 | Johnston et al. | |
| 7,258,663 B2 | 8/2007 | Doguchi et al. | |
| 7,261,687 B2 | 8/2007 | Yang | |
| 7,280,139 B2 | 10/2007 | Pahr et al. | |
| 7,298,938 B2 | 11/2007 | Johnston | |
| 7,312,879 B2 | 12/2007 | Johnston | |
| 7,319,478 B2 | 1/2008 | Dolt et al. | |
| 7,355,155 B2 | 4/2008 | Wang | |
| 7,356,198 B2 | 4/2008 | Chauville et al. | |
| 7,365,768 B1 | 4/2008 | Ono et al. | |
| 7,369,140 B1 | 5/2008 | King et al. | |
| 7,369,176 B2 | 5/2008 | Sonnenschein et al. | |
| 7,385,708 B2 | 6/2008 | Ackerman et al. | |
| 7,455,638 B2 | 11/2008 | Ogawa et al. | |
| 7,470,229 B2 | 12/2008 | Ogawa et al. | |
| 7,476,197 B2 | 1/2009 | Wiklof et al. | |
| 7,532,760 B2 | 5/2009 | Kaplinsky et al. | |
| 7,540,645 B2 | 5/2009 | Choi | |
| 7,544,163 B2 | 6/2009 | MacKinnon et al. | |
| 7,545,434 B2 | 6/2009 | Bean et al. | |
| 7,564,935 B2 | 7/2009 | Suzuki | |
| 7,567,291 B2 | 7/2009 | Bechtel et al. | |
| 7,573,516 B2 | 8/2009 | Krymski et al. | |
| 7,573,519 B2 | 8/2009 | Phan et al. | |
| 7,583,872 B2 | 9/2009 | Seibel et al. | |
| 7,608,807 B2 | 10/2009 | Hick et al. | |
| 7,616,238 B2 | 11/2009 | Avni et al. | |
| 7,630,008 B2 | 12/2009 | Sarwari | |
| 7,744,528 B2 | 6/2010 | Wallace et al. | |
| 7,760,258 B2 | 7/2010 | Huang et al. | |
| 7,783,133 B2 | 8/2010 | Dunki-Jacobs et al. | |
| 7,784,697 B2 | 8/2010 | Johnston et al. | |
| 7,791,009 B2 | 9/2010 | Johnston et al. | |
| 7,792,378 B2 | 9/2010 | Liege et al. | |
| 7,794,394 B2 | 9/2010 | Frangioni | |
| 7,796,870 B2 | 9/2010 | Wang | |
| 7,813,538 B2 | 10/2010 | Carroll et al. | |
| 7,901,974 B2 | 3/2011 | Venezia et al. | |
| 7,914,447 B2 | 3/2011 | Kanai | |
| 7,916,193 B2 | 3/2011 | Fossum | |
| 7,935,050 B2 | 5/2011 | Luanava et al. | |
| 7,944,566 B2 | 5/2011 | Xie | |
| 7,952,096 B2 | 5/2011 | Rhodes | |
| 7,969,097 B2 | 6/2011 | Van De Ven | |
| 7,995,123 B2 | 8/2011 | Lee et al. | |
| 8,018,589 B2 | 9/2011 | MacKinnon et al. | |
| 8,040,394 B2 | 10/2011 | Fossum et al. | |
| 8,054,339 B2 | 11/2011 | Fossum et al. | |
| 8,059,174 B2 | 11/2011 | Mann et al. | |
| 8,100,826 B2 | 1/2012 | MacKinnon et al. | |
| 8,159,584 B2 | 4/2012 | Iwabuchi et al. | |
| 8,193,542 B2 | 6/2012 | Machara | |
| 8,194,061 B2 | 6/2012 | Wang et al. | |
| 8,212,884 B2 | 7/2012 | Seibel et al. | |
| 8,213,698 B2 | 7/2012 | Wang | |
| 8,231,522 B2 | 7/2012 | Endo et al. | |
| 8,300,111 B2 | 10/2012 | Iwane | |
| 8,372,003 B2 | 2/2013 | St. George et al. | |
| 8,382,662 B2 | 2/2013 | Soper et al. | |
| 8,396,535 B2 | 3/2013 | Wang et al. | |
| 8,423,110 B2 | 4/2013 | Barbato et al. | |
| 8,471,938 B2 | 6/2013 | Altice, Jr. et al. | |
| 8,476,575 B2 | 7/2013 | Mokhuatyuk | |
| 8,482,823 B2 | 7/2013 | Cheng | |
| 8,493,474 B2 | 7/2013 | Richardson | |
| 8,493,564 B2 | 7/2013 | Brukilacchio et al. | |
| 8,523,367 B2 | 9/2013 | Ogura | |
| 8,537,203 B2 | 9/2013 | Seibel et al. | |
| 8,559,743 B2 | 10/2013 | Liege et al. | |
| 8,582,011 B2 | 11/2013 | Dosluoglu | |
| 8,602,971 B2 | 12/2013 | Farr | |
| 8,605,177 B2 | 12/2013 | Rossi et al. | |

(56) References Cited

U.S. PATENT DOCUMENTS

| | | |
|---|---|---|
| 8,610,808 B2 | 12/2013 | Prescher et al. |
| 8,614,754 B2 | 12/2013 | Fossum |
| 8,625,016 B2 | 1/2014 | Fossum et al. |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,836,834 B2 | 9/2014 | Hashimoto et al. |
| 8,848,063 B2 | 9/2014 | Jo et al. |
| 8,858,425 B2 | 10/2014 | Farr et al. |
| 8,885,034 B2 | 11/2014 | Adair et al. |
| 8,941,308 B2 | 1/2015 | Briggs |
| 9,182,337 B2 | 11/2015 | Kamee et al. |
| 9,349,764 B1 | 5/2016 | Lee et al. |
| 9,509,917 B2 | 11/2016 | Blanquart et al. |
| 9,516,239 B2 | 12/2016 | Blanquart et al. |
| 9,634,878 B1 | 4/2017 | Bench et al. |
| 9,762,879 B2 | 9/2017 | Blanquart et al. |
| 9,777,913 B2 | 10/2017 | Talbert et al. |
| 10,084,944 B2 | 9/2018 | Henley et al. |
| 10,251,530 B2 | 4/2019 | Henley et al. |
| 10,277,875 B2 | 4/2019 | Blanquart et al. |
| 10,568,496 B2 | 2/2020 | Blanquart et al. |
| 10,785,461 B2 | 9/2020 | Blanquart et al. |
| 10,911,649 B2 | 2/2021 | Henley et al. |
| 10,917,562 B2 | 2/2021 | Richardson et al. |
| 11,070,779 B2 | 7/2021 | Blanquart et al. |
| 2001/0016064 A1* | 8/2001 | Tsuruoka ............... H04N 1/407 382/167 |
| 2001/0017649 A1 | 8/2001 | Yaron |
| 2001/0030744 A1 | 10/2001 | Chang |
| 2001/0055462 A1 | 12/2001 | Seibel |
| 2002/0045801 A1 | 4/2002 | Niida et al. |
| 2002/0054219 A1 | 5/2002 | Jaspers |
| 2002/0064341 A1 | 5/2002 | Fauver et al. |
| 2002/0080248 A1 | 6/2002 | Adair et al. |
| 2002/0080359 A1 | 6/2002 | Denk et al. |
| 2002/0140844 A1 | 10/2002 | Kurokawa et al. |
| 2002/0158976 A1 | 10/2002 | Vni et al. |
| 2002/0158986 A1 | 10/2002 | Baer |
| 2003/0007087 A1 | 1/2003 | Hakamata et al. |
| 2003/0007686 A1 | 1/2003 | Roever |
| 2003/0107664 A1 | 6/2003 | Suzuki |
| 2003/0112507 A1 | 6/2003 | Divelbiss et al. |
| 2003/0189663 A1 | 10/2003 | Dolt et al. |
| 2003/0189705 A1 | 10/2003 | Pardo |
| 2004/0082833 A1 | 4/2004 | Adler et al. |
| 2004/0170712 A1 | 9/2004 | Sadek El Mogy |
| 2004/0215059 A1 | 10/2004 | Homan et al. |
| 2005/0009982 A1 | 1/2005 | Inagaki et al. |
| 2005/0010081 A1 | 1/2005 | Doguchi et al. |
| 2005/0027164 A1 | 2/2005 | Barbato et al. |
| 2005/0038322 A1 | 2/2005 | Banik |
| 2005/0041571 A1 | 2/2005 | Ichihara et al. |
| 2005/0052680 A1 | 3/2005 | Okamura |
| 2005/0113641 A1 | 5/2005 | Bala |
| 2005/0122530 A1 | 6/2005 | Denk et al. |
| 2005/0151866 A1 | 7/2005 | Ando et al. |
| 2005/0169375 A1 | 8/2005 | Pai et al. |
| 2005/0200291 A1 | 9/2005 | Naugler, Jr. et al. |
| 2005/0234302 A1 | 10/2005 | MacKinnon et al. |
| 2005/0237384 A1 | 10/2005 | Jess et al. |
| 2005/0261552 A1 | 11/2005 | Mori et al. |
| 2005/0267328 A1 | 12/2005 | Blumzvig et al. |
| 2005/0267329 A1 | 12/2005 | Konstorum et al. |
| 2005/0277808 A1 | 12/2005 | Sonnenschein et al. |
| 2005/0288546 A1 | 12/2005 | Sonnenschein et al. |
| 2006/0038823 A1 | 2/2006 | Arcas |
| 2006/0069314 A1 | 3/2006 | Farr |
| 2006/0087841 A1 | 4/2006 | Chern et al. |
| 2006/0106284 A1 | 5/2006 | Shouji et al. |
| 2006/0197664 A1 | 9/2006 | Zhang et al. |
| 2006/0202036 A1 | 9/2006 | Wang et al. |
| 2006/0221250 A1 | 10/2006 | Rossbach et al. |
| 2006/0226231 A1 | 10/2006 | Johnston et al. |
| 2006/0264734 A1 | 11/2006 | Kimoto et al. |
| 2006/0274335 A1* | 12/2006 | Wittenstein ............... H04N 9/67 358/1.9 |
| 2007/0010712 A1 | 1/2007 | Negishi |
| 2007/0010713 A1 | 1/2007 | Negishi |
| 2007/0029629 A1 | 2/2007 | Yazdi |
| 2007/0041448 A1* | 2/2007 | Miller ............... H04N 19/61 375/240.18 |
| 2007/0066868 A1 | 3/2007 | Shikii |
| 2007/0083085 A1 | 4/2007 | Birnkrant et al. |
| 2007/0092283 A1 | 4/2007 | Sugihara |
| 2007/0129601 A1 | 6/2007 | Johnston et al. |
| 2007/0147033 A1 | 6/2007 | Ogawa et al. |
| 2007/0182723 A1 | 8/2007 | Imai et al. |
| 2007/0182842 A1 | 8/2007 | Sonnenschein et al. |
| 2007/0225560 A1 | 9/2007 | Avni et al. |
| 2007/0244364 A1 | 10/2007 | Luanava et al. |
| 2007/0244365 A1 | 10/2007 | Wiklof |
| 2007/0274649 A1 | 11/2007 | Takahashi et al. |
| 2007/0276187 A1 | 11/2007 | Wiklof et al. |
| 2007/0279486 A1 | 12/2007 | Bayer et al. |
| 2007/0285526 A1 | 12/2007 | Mann et al. |
| 2007/0293720 A1 | 12/2007 | Bayer |
| 2008/0045800 A2 | 2/2008 | Farr |
| 2008/0049132 A1 | 2/2008 | Suzuki |
| 2008/0088719 A1 | 4/2008 | Jacob et al. |
| 2008/0107333 A1 | 5/2008 | Mazinani et al. |
| 2008/0136953 A1 | 6/2008 | Barnea et al. |
| 2008/0158348 A1 | 7/2008 | Karpen et al. |
| 2008/0164550 A1 | 7/2008 | Chen et al. |
| 2008/0165360 A1 | 7/2008 | Johnston |
| 2008/0167523 A1 | 7/2008 | Uchiyama et al. |
| 2008/0192131 A1 | 8/2008 | Kim et al. |
| 2008/0208077 A1 | 8/2008 | Iddan et al. |
| 2008/0218598 A1 | 9/2008 | Harada et al. |
| 2008/0218615 A1 | 9/2008 | Huang et al. |
| 2008/0218824 A1 | 9/2008 | Johnston et al. |
| 2008/0249369 A1 | 10/2008 | Seibel et al. |
| 2008/0287742 A1 | 11/2008 | St. George et al. |
| 2009/0012361 A1 | 1/2009 | MacKinnon et al. |
| 2009/0012368 A1 | 1/2009 | Banik |
| 2009/0021588 A1 | 1/2009 | Border et al. |
| 2009/0021618 A1 | 1/2009 | Schwarz et al. |
| 2009/0024000 A1 | 1/2009 | Chen |
| 2009/0028465 A1 | 1/2009 | Pan |
| 2009/0074265 A1 | 3/2009 | Huang et al. |
| 2009/0091645 A1 | 4/2009 | Trimeche et al. |
| 2009/0137893 A1 | 5/2009 | Seibel et al. |
| 2009/0147077 A1 | 6/2009 | Tani et al. |
| 2009/0154886 A1 | 6/2009 | Lewis et al. |
| 2009/0160976 A1 | 6/2009 | Chen et al. |
| 2009/0189530 A1 | 7/2009 | Ashdown et al. |
| 2009/0208143 A1 | 8/2009 | Yoon et al. |
| 2009/0227847 A1 | 9/2009 | Tepper et al. |
| 2009/0232213 A1 | 9/2009 | Jia |
| 2009/0259102 A1 | 10/2009 | Koninckx et al. |
| 2009/0268063 A1 | 10/2009 | Ellis-Monaghan et al. |
| 2009/0274380 A1 | 11/2009 | Wedi |
| 2009/0292168 A1 | 11/2009 | Farr |
| 2009/0309500 A1 | 12/2009 | Reisch |
| 2009/0316116 A1 | 12/2009 | Melville et al. |
| 2009/0322912 A1 | 12/2009 | Blanquart |
| 2010/0004513 A1 | 1/2010 | MacKinnon et al. |
| 2010/0026722 A1 | 2/2010 | Kondo |
| 2010/0049180 A1 | 2/2010 | Wells et al. |
| 2010/0069713 A1 | 3/2010 | Endo et al. |
| 2010/0092151 A1* | 4/2010 | Miyakoshi ............... H04N 5/147 386/343 |
| 2010/0102199 A1 | 4/2010 | Negley et al. |
| 2010/0121142 A1 | 5/2010 | OuYang et al. |
| 2010/0121143 A1 | 5/2010 | Sugimoto et al. |
| 2010/0123775 A1 | 5/2010 | Shibasaki |
| 2010/0134608 A1 | 6/2010 | Shibasaki |
| 2010/0134662 A1 | 6/2010 | Bub |
| 2010/0135398 A1 | 6/2010 | Wittmann et al. |
| 2010/0137684 A1 | 6/2010 | Shibasaki et al. |
| 2010/0149421 A1 | 6/2010 | Lin et al. |

(56) References Cited

U.S. PATENT DOCUMENTS

| | | | |
|---|---|---|---|
| 2010/0157037 A1 | 6/2010 | Iketani et al. |
| 2010/0157039 A1 | 6/2010 | Sugai |
| 2010/0165087 A1 | 7/2010 | Corso et al. |
| 2010/0171429 A1 | 7/2010 | Garcia et al. |
| 2010/0182446 A1 | 7/2010 | Matsubayashi |
| 2010/0198009 A1 | 8/2010 | Farr et al. |
| 2010/0198134 A1 | 8/2010 | Eckhouse et al. |
| 2010/0201797 A1 | 8/2010 | Shizukuishi et al. |
| 2010/0208056 A1 | 8/2010 | Olsson et al. |
| 2010/0228089 A1 | 9/2010 | Hoffman et al. |
| 2010/0261961 A1 | 10/2010 | Scott et al. |
| 2010/0274082 A1 | 10/2010 | Iguchi et al. |
| 2010/0274090 A1 | 10/2010 | Ozaki et al. |
| 2010/0305406 A1 | 12/2010 | Braun et al. |
| 2010/0309333 A1 | 12/2010 | Smith et al. |
| 2011/0028790 A1 | 2/2011 | Farr et al. |
| 2011/0034769 A1 | 2/2011 | Adair et al. |
| 2011/0051390 A1 | 3/2011 | Lin et al. |
| 2011/0063483 A1 | 3/2011 | Rossi et al. |
| 2011/0122301 A1 | 5/2011 | Yamura et al. |
| 2011/0149358 A1* | 6/2011 | Cheng ............... H04N 1/58 358/475 |
| 2011/0181709 A1 | 7/2011 | Wright et al. |
| 2011/0181840 A1 | 7/2011 | Cobb |
| 2011/0184239 A1 | 7/2011 | Wright et al. |
| 2011/0184243 A1 | 7/2011 | Wright et al. |
| 2011/0208004 A1 | 8/2011 | Feingold et al. |
| 2011/0212649 A1 | 9/2011 | Stokoe et al. |
| 2011/0237882 A1 | 9/2011 | Saito |
| 2011/0237884 A1 | 9/2011 | Saito |
| 2011/0245605 A1 | 10/2011 | Jacobsen et al. |
| 2011/0245616 A1 | 10/2011 | Kobayashi |
| 2011/0255844 A1 | 10/2011 | Wu et al. |
| 2011/0274175 A1 | 11/2011 | Sumitomo |
| 2011/0279679 A1 | 11/2011 | Samuel et al. |
| 2011/0288374 A1 | 11/2011 | Hadani et al. |
| 2011/0291564 A1 | 12/2011 | Huang |
| 2011/0292258 A1 | 12/2011 | Adler et al. |
| 2011/0295061 A1 | 12/2011 | Haramaty et al. |
| 2012/0004508 A1 | 1/2012 | McDowall et al. |
| 2012/0014563 A1 | 1/2012 | Bendall |
| 2012/0016200 A1 | 1/2012 | Seto et al. |
| 2012/0029279 A1 | 2/2012 | Kucklick |
| 2012/0033118 A1 | 2/2012 | Lee et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0078052 A1 | 3/2012 | Cheng |
| 2012/0098933 A1 | 4/2012 | Robinson et al. |
| 2012/0104230 A1 | 5/2012 | Eismann et al. |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0155761 A1 | 6/2012 | Matsuoka |
| 2012/0157774 A1 | 6/2012 | Kaku |
| 2012/0172665 A1 | 7/2012 | Alyn et al. |
| 2012/0194686 A1 | 8/2012 | Liu et al. |
| 2012/0197080 A1 | 8/2012 | Murayama |
| 2012/0200685 A1 | 8/2012 | Kawasaki et al. |
| 2012/0209071 A1 | 8/2012 | Bayer et al. |
| 2012/0242975 A1 | 9/2012 | Min et al. |
| 2012/0262621 A1 | 10/2012 | Sato et al. |
| 2012/0281111 A1 | 11/2012 | Jo et al. |
| 2012/0296238 A1 | 11/2012 | Chernov et al. |
| 2012/0319586 A1 | 12/2012 | Riesebosch |
| 2012/0327270 A1 | 12/2012 | Shirakawa et al. |
| 2013/0016200 A1 | 1/2013 | Ovod |
| 2013/0018256 A1 | 1/2013 | Kislev et al. |
| 2013/0035545 A1 | 2/2013 | Ono |
| 2013/0053642 A1 | 2/2013 | Mizuyoshi et al. |
| 2013/0070071 A1 | 3/2013 | Peltie et al. |
| 2013/0126708 A1 | 5/2013 | Blanquart |
| 2013/0127934 A1 | 5/2013 | Chiang |
| 2013/0135589 A1 | 5/2013 | Curtis et al. |
| 2013/0144120 A1 | 6/2013 | Yamazaki |
| 2013/0155215 A1 | 6/2013 | Shimada et al. |
| 2013/0155305 A1 | 6/2013 | Shintani |
| 2013/0158346 A1 | 6/2013 | Soper et al. |
| 2013/0184524 A1 | 7/2013 | Shimada et al. |
| 2013/0211217 A1 | 8/2013 | Yamaguchi et al. |
| 2013/0242069 A1 | 9/2013 | Kobayashi |
| 2013/0244453 A1 | 9/2013 | Sakamoto |
| 2013/0274597 A1 | 10/2013 | Byrne et al. |
| 2013/0289347 A1 | 10/2013 | Ito et al. |
| 2013/0292571 A1 | 11/2013 | Mukherjee et al. |
| 2013/0296651 A1 | 11/2013 | Ito et al. |
| 2013/0296652 A1 | 11/2013 | Farr |
| 2013/0300837 A1 | 11/2013 | DiCarlo et al. |
| 2013/0342690 A1 | 12/2013 | Williams et al. |
| 2014/0012078 A1 | 1/2014 | Coussa |
| 2014/0022365 A1 | 1/2014 | Yoshino |
| 2014/0031623 A1 | 1/2014 | Kagaya |
| 2014/0005532 A1 | 2/2014 | Choi et al. |
| 2014/0052004 A1 | 2/2014 | D'Alfonso et al. |
| 2014/0066711 A1 | 3/2014 | Farin et al. |
| 2014/0073852 A1 | 3/2014 | Banik et al. |
| 2014/0073853 A1 | 3/2014 | Swisher et al. |
| 2014/0078278 A1 | 3/2014 | Lei |
| 2014/0088363 A1 | 3/2014 | Sakai et al. |
| 2014/0094649 A1 | 4/2014 | Ito |
| 2014/0104466 A1 | 4/2014 | Fossum |
| 2014/0110485 A1 | 4/2014 | Toa et al. |
| 2014/0142383 A1 | 5/2014 | Blumenzweig et al. |
| 2014/0160318 A1 | 6/2014 | Blanquart et al. |
| 2014/0163319 A1 | 6/2014 | Blanquart et al. |
| 2014/0198249 A1 | 7/2014 | Tanaka et al. |
| 2014/0203084 A1 | 7/2014 | Wang |
| 2014/0225215 A1 | 8/2014 | Chien et al. |
| 2014/0267655 A1 | 9/2014 | Richardson et al. |
| 2014/0267851 A1 | 9/2014 | Rhoads |
| 2014/0267890 A1 | 9/2014 | Lelescu et al. |
| 2014/0268860 A1 | 9/2014 | Talbert et al. |
| 2014/0275764 A1 | 9/2014 | Shen et al. |
| 2014/0288365 A1 | 9/2014 | Henley et al. |
| 2014/0300698 A1 | 10/2014 | Wany |
| 2014/0316197 A1 | 10/2014 | St. George et al. |
| 2014/0316199 A1 | 10/2014 | Kucklick |
| 2014/0354788 A1 | 12/2014 | Yano |
| 2014/0364689 A1 | 12/2014 | Adair et al. |
| 2015/0023611 A1 | 1/2015 | Salvador et al. |
| 2015/0237245 A1 | 8/2015 | Renard et al. |
| 2015/0271370 A1 | 9/2015 | Henley et al. |
| 2016/0183775 A1 | 6/2016 | Blanquart et al. |
| 2017/0085853 A1 | 3/2017 | Blanquart et al. |
| 2017/0230574 A1 | 8/2017 | Richardson et al. |
| 2019/0028621 A1 | 1/2019 | Henley et al. |
| 2019/0133416 A1 | 5/2019 | Henley et al. |
| 2019/0174058 A1 | 6/2019 | Richardson et al. |
| 2019/0197712 A1 | 6/2019 | Talbert et al. |
| 2019/0200906 A1 | 7/2019 | Shelton, IV et al. |
| 2019/0253685 A1 | 8/2019 | Blanquart et al. |
| 2020/0292160 A1 | 9/2020 | Talbert et al. |

FOREIGN PATENT DOCUMENTS

| | | |
|---|---|---|
| CN | 201239130 Y | 5/2009 |
| CN | 101449575 A | 6/2009 |
| CN | 101634749 A | 1/2010 |
| CN | 101755448 A | 6/2010 |
| CN | 102469932 A | 5/2012 |
| CN | 103185960 A | 7/2013 |
| EP | 0660616 A2 | 6/1995 |
| EP | 0904725 A1 | 3/1999 |
| EP | 1079255 A2 | 2/2001 |
| EP | 1116473 A2 | 7/2001 |
| EP | 1637062 A1 | 3/2006 |
| EP | 1712177 A1 | 10/2006 |
| EP | 1819151 A1 | 8/2007 |
| EP | 2359739 A1 | 8/2011 |
| EP | 2371268 A1 | 8/2011 |
| EP | 2478693 A1 | 7/2012 |
| EP | 3459431 A1 | 3/2014 |
| IL | 236893 B | 8/2020 |
| JP | H04-039789 | 4/1992 |

(56) References Cited

FOREIGN PATENT DOCUMENTS

| | | |
|---|---|---|
| JP | H07-240931 | 9/1995 |
| JP | 1995-240931 | 3/1997 |
| JP | 2000-051150 A | 2/2000 |
| JP | 200-199863 A | 7/2000 |
| JP | 2000270230 | 9/2000 |
| JP | 2001190489 A | 7/2001 |
| JP | 2001-308531 A | 11/2001 |
| JP | 2002-020816 A | 1/2002 |
| JP | 2002-028125 A | 1/2002 |
| JP | 2002-045329 A | 2/2002 |
| JP | 2002-112961 A | 4/2002 |
| JP | 2005-204741 A | 8/2005 |
| JP | 2007-029746 A | 2/2007 |
| JP | 2007143963 A | 6/2007 |
| JP | 2007-240931 A | 9/2007 |
| JP | 2008514304 | 5/2008 |
| JP | 2008-153313 A | 7/2008 |
| JP | 2008264539 A | 11/2008 |
| JP | 2008295929 A | 12/2008 |
| JP | 2009-537283 A | 10/2009 |
| JP | 2010-17377 A | 1/2010 |
| JP | 2010-068992 A | 4/2010 |
| JP | 2010-125284 A | 6/2010 |
| JP | 2010-158415 A | 7/2010 |
| JP | 2011-055327 A | 3/2011 |
| JP | 2011514605 | 5/2011 |
| JP | 2011514605 A | 5/2011 |
| JP | 2012-000160 A | 1/2012 |
| JP | 2012024450 | 2/2012 |
| JP | 2013-27432 A | 2/2013 |
| JP | 2011-267098 A | 6/2013 |
| JP | 2014514782 | 6/2014 |
| JP | 5682812 B2 | 1/2015 |
| JP | 2015525642 | 9/2015 |
| JP | A61-62440 | 6/2017 |
| JP | 6804488 B2 | 12/2020 |
| MX | 2015001195 A | 1/2016 |
| MX | 346174 | 3/2017 |
| WO | 1996005693 | 2/1996 |
| WO | 2006037034 A2 | 4/2006 |
| WO | 2009120228 A1 | 1/2009 |
| WO | 2009018613 A1 | 2/2009 |
| WO | 2009045235 A2 | 4/2009 |
| WO | 2009115885 A2 | 9/2009 |
| WO | 2009120228 A1 | 10/2009 |
| WO | 2012043771 A1 | 4/2012 |
| WO | 2012043771 A1 | 5/2012 |
| WO | 2012137845 A1 | 10/2012 |

OTHER PUBLICATIONS

Jack, Keith "Video Demystified: A Handbook for the Digital Engineer," 2007 Fifth Edition. ISBN: 978-0-7506-8395-1, p. 21.

* cited by examiner

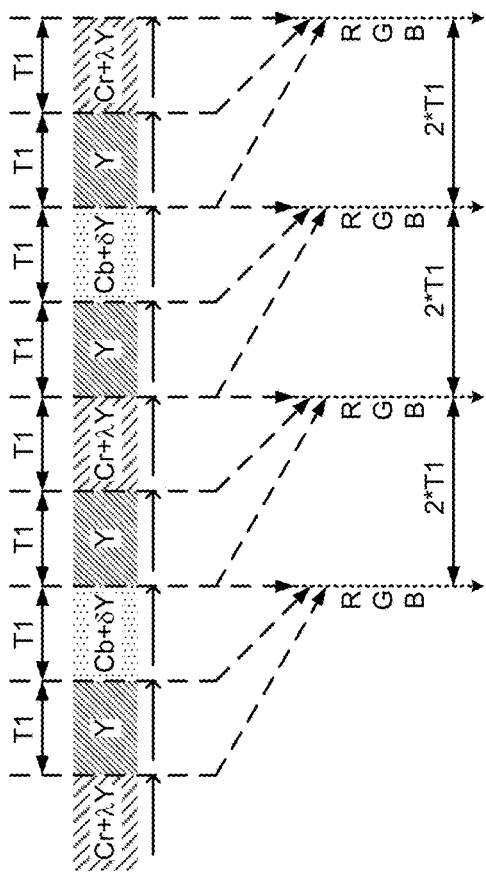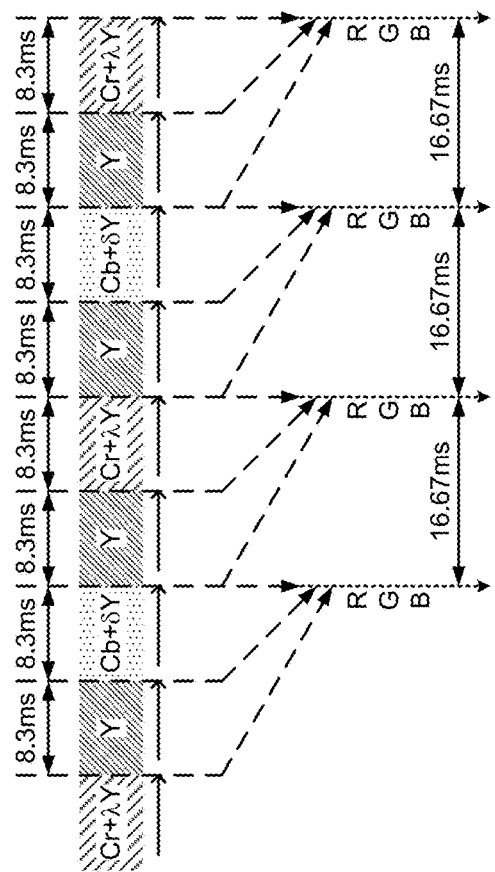

YCBCR PULSED ILLUMINATION SCHEME IN A LIGHT DEFICIENT ENVIRONMENT

CROSS-REFERENCE TO RELATED APPLICATIONS

This application is a continuation of U.S. application Ser. No. 16/940,189, filed Jul. 27, 2020, which is a continuation of U.S. application Ser. No. 16/398,114, filed Apr. 29, 2019, which is a continuation of U.S. application Ser. No. 15/701,264, filed on Sep. 11, 2017 (now U.S. Pat. No. 10,277,875), which is a continuation of U.S. application Ser. No. 15/369,170, filed on Dec. 5, 2016 (now U.S. Pat. No. 9,762,879, issued Sep. 12, 2017), which is a division of U.S. application Ser. No. 13/952,570, filed on Jul. 26, 2013 (now U.S. Pat. No. 9,516,239, issued Dec. 6, 2016) and claims the benefit of U.S. Provisional Patent Application No. 61/676,289, filed on Jul. 26, 2012, and U.S. Provisional Patent Application No. 61/790,487, filed on Mar. 15, 2013, and U.S. Provisional Patent Application No. 61/790,719, filed on Mar. 15, 2013 and U.S. Provisional Patent Application No. 61/791,473, filed on Mar. 15, 2013, which are hereby incorporated by reference herein in their entireties, including but not limited to those portions that specifically appear hereinafter, the incorporation by reference being made with the following exception: In the event that any portion of the above-referenced applications is inconsistent with this application, this application supersedes said above-referenced applications.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to electromagnetic sensing and sensors in relation to creating a video stream having chrominance and luminance pulses from a controlled light source. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out herein.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings.

FIG. 12A illustrates a graphical representation of the operation of a pixel array in accordance with the principles and teachings of the disclosure;

FIG. 12B illustrates a graphical representation of the operation of a pixel array in accordance with the principles and teachings of the disclosure;

DETAILED DESCRIPTION

Figure 1:
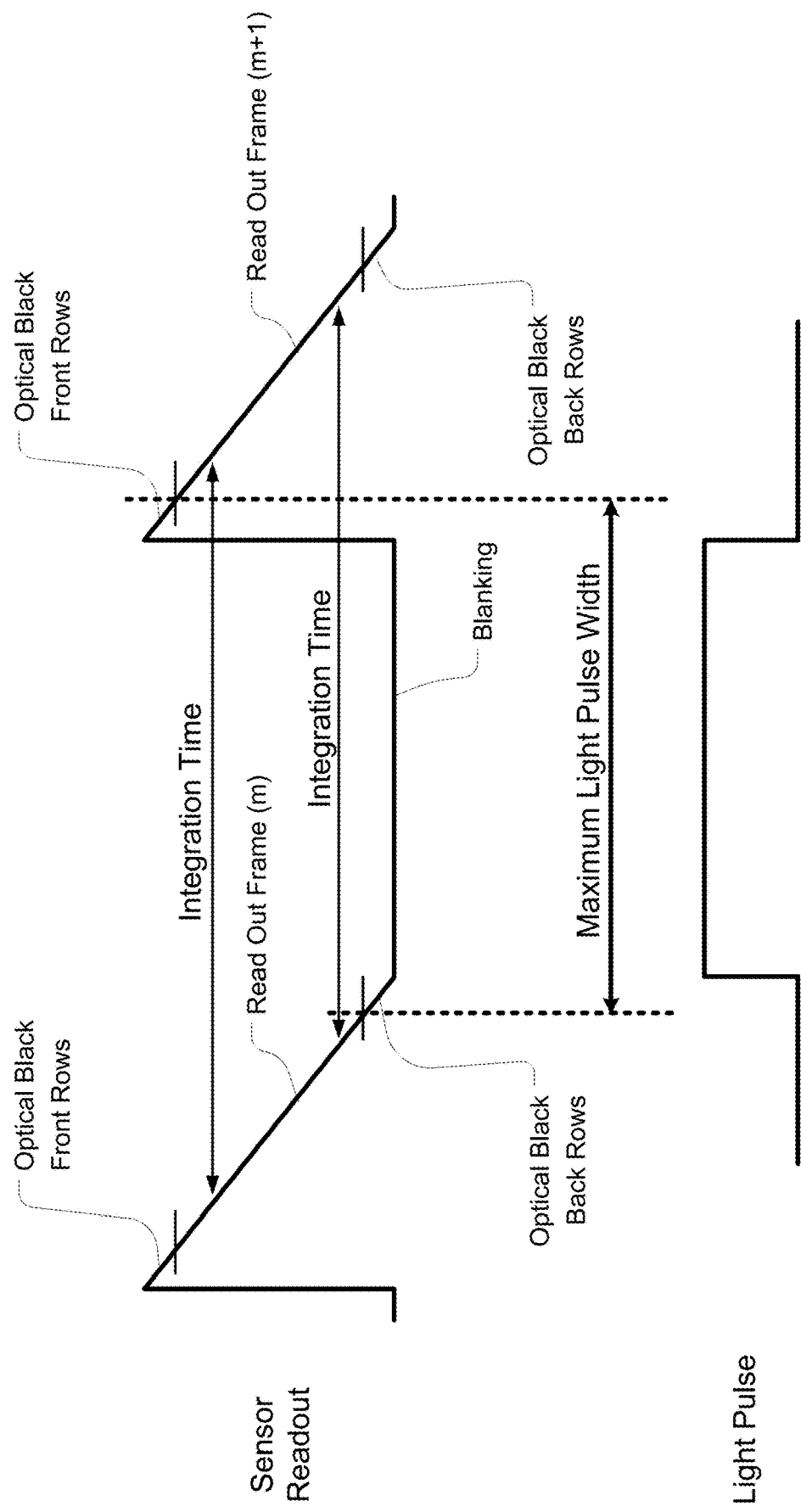
FIG. 1 illustrates a graphical representation of the operation of a pixel array in accordance with the principles and teachings of the disclosure.

The disclosure extends to methods, systems, and computer based products for digital imaging that may be primarily suited to medical applications. In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

Luminance-chrominance based color spaces date back to the advent of color television, when color image transmission was required to be compatible with older monochrome CRTs. The luminance component corresponds to the (color-agnostic) brightness aspect of the image data. The color information is carried in the remaining two channels. The separation of image data into the luminance and chrominance components is still an important process in modern digital imaging systems, since it is closely related to the human visual system.

The human retina contains arrays of two basic photoreceptor cell types; rods and cones. The rods provide the brightness information and have about a factor-20 greater overall spatial density than the cones. The cones are much less sensitive and there are three basic types, having peak responses at three different wavelengths. The spectral response of the rods, which peaks in the green region, is the basis for computing luminance color-space conversion coefficients. Since rods have the greater density, the spatial resolution of an image representation is much more important for the luminance component than for either chrominance component. Camera designers and image processing engineers seek to account for this fact in several ways, e.g., by spatially filtering the chrominance channels to reduce noise and by affording greater relative system bandwidth to luminance data.

In describing the subject matter of the disclosure, the following terminology will be used in accordance with the definitions set out below.

It must be noted that, as used in this specification, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified.

As used herein, the phrase "consisting essentially of" and grammatical equivalents thereof limit the scope of a claim, if any, to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

Referring now to the figures, FIG. 1 illustrates the basic timing of single frame capture by a conventional CMOS sensor. Co-pending U.S. patent application Ser. No. 13/952,518 entitled CONTINUOUS VIDEO IN A LIGHT DEFICIENT ENVIRONMENT is hereby incorporated by this reference into this disclosure as if fully set forth herein. It will be appreciated that the x direction corresponds to time and the diagonal lines indicate the activity of an internal pointer that reads out each frame of data, one line at time. The same pointer is responsible for resetting each row of pixels for the next exposure period. The net integration time for each row is equivalent, but they are staggered in time with respect to one another due to the rolling reset and read process. Therefore, for any scenario in which adjacent frames are required to represent different constitutions of light, the only option for having each row be consistent is to pulse the light between the readout cycles. More specifically, the maximum available period corresponds to the sum of the blanking time plus any time during which optical black or optically blind (OB) rows are serviced at the start or end of the frame.

Figure 2:
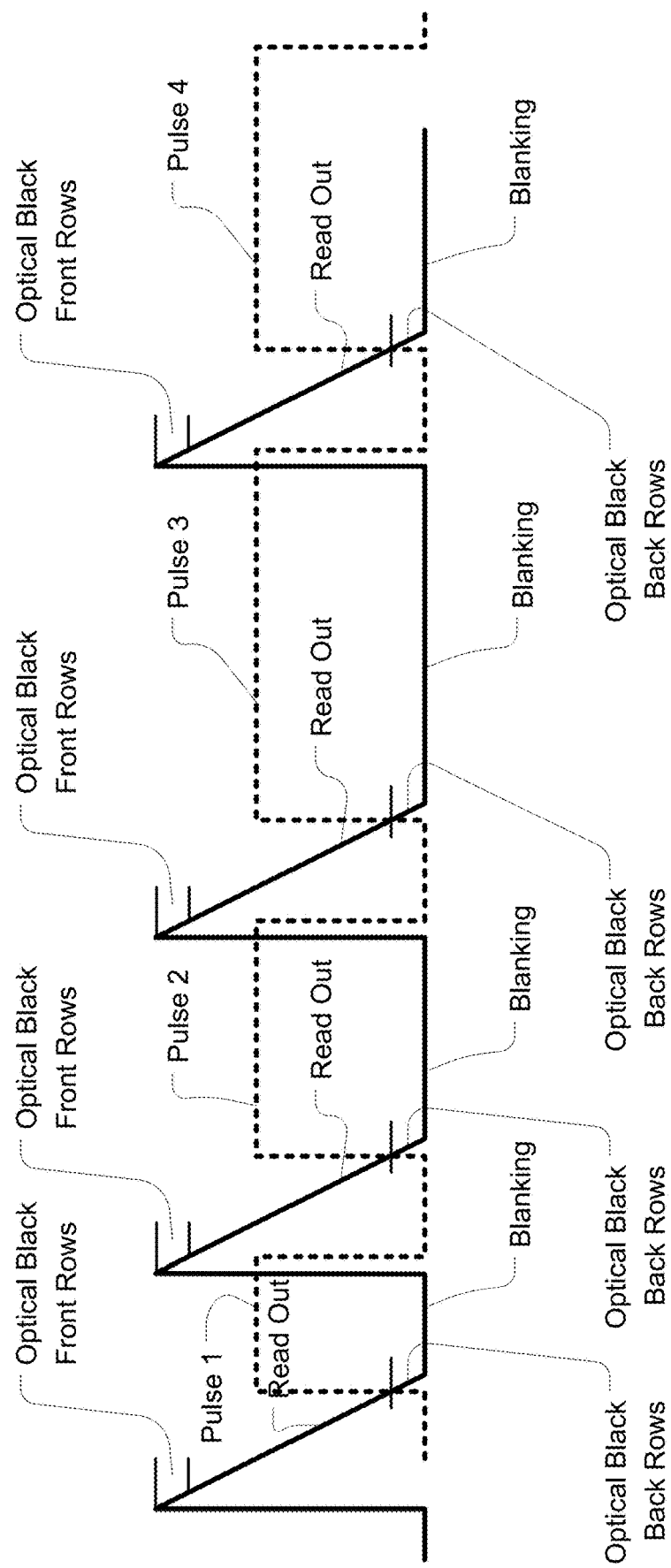
FIG. 2 illustrates a graphical representation of a pixel array for a plurality of frames in accordance with the principles and teachings of the disclosure.

An example illumination sequence is a repeating pattern of four frames (R-G-B-G). As for the Bayer pattern of color filters, this provides for greater luminance detail than chrominance. This approach is accomplished by strobing the scene with either laser or light-emitting diodes at high speed, under the control of the camera system, and by virtue of a specially designed CMOS sensor with high speed readout. The principal benefit is that the sensor can accomplish the same spatial resolution with significantly fewer pixels compared with conventional Bayer or 3-sensor cameras. Therefore, the physical space occupied by the pixel array may be reduced. The actual pulse periods may differ within the repeating pattern, as illustrated in FIG. 2. This is useful for, e.g., apportioning greater time to the components that require the greater light energy or those having the weaker sources. As long as the average captured frame rate is an integer multiple of the requisite final system frame rate, the data may simply be buffered in the signal processing chain as appropriate.

The facility to reduce the CMOS sensor chip-area to the extent allowed by combining all of these methods is particularly attractive for small diameter (~3-10 mm) endoscopy. In particular, it allows for endoscope designs in which the sensor is located in the space-constrained distal end, thereby greatly reducing the complexity and cost of the optical section, while providing high definition video. A consequence of this approach is that to reconstruct each final, full color image, requires that data be fused from three separate snapshots in time. Any motion within the scene, relative to the optical frame of reference of the endoscope, will generally degrade the perceived resolution, since the edges of objects appear at slightly different locations within each captured component. In this disclosure, a means of diminishing this issue is described which exploits the fact that spatial resolution is much more important for luminance information, than for chrominance.

The basis of the approach is that, instead of firing monochromatic light during each frame, combinations of the three wavelengths are used to provide all of the luminance information within a single image. The chrominance information is derived from separate frames with, e.g., a repeating pattern such as Y-Cb-Y-Cr. While it is possible to provide pure luminance data by a shrewd choice of pulse ratios, the same is not true of chrominance. However, a workaround for this is presented in this disclosure.

Figure 3A:
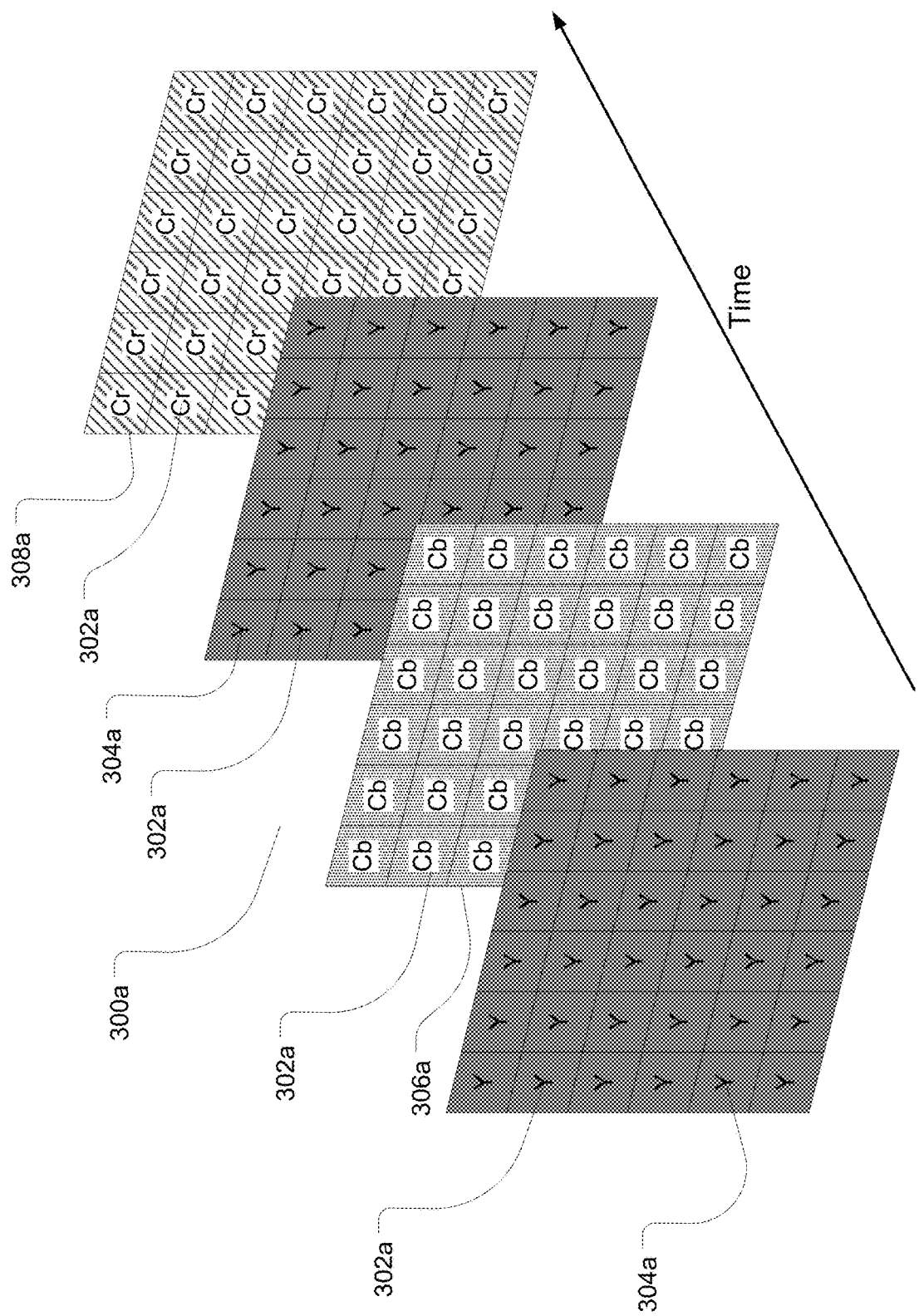
FIG. 3A illustrates a schematic of an embodiment of an operation sequence of chrominance and luminance frames in accordance with the principles and teachings of the disclosure.

In an embodiment, as illustrated in FIG. 3A, an endoscopic system 300a may comprise a pixel array 302a having uniform pixels and the system 300a may be operated to receive Y (luminance pulse) 304a, Cb (ChromaBlue) 306a and Cr (ChromaRed) 308a pulses.

Figure 3B:
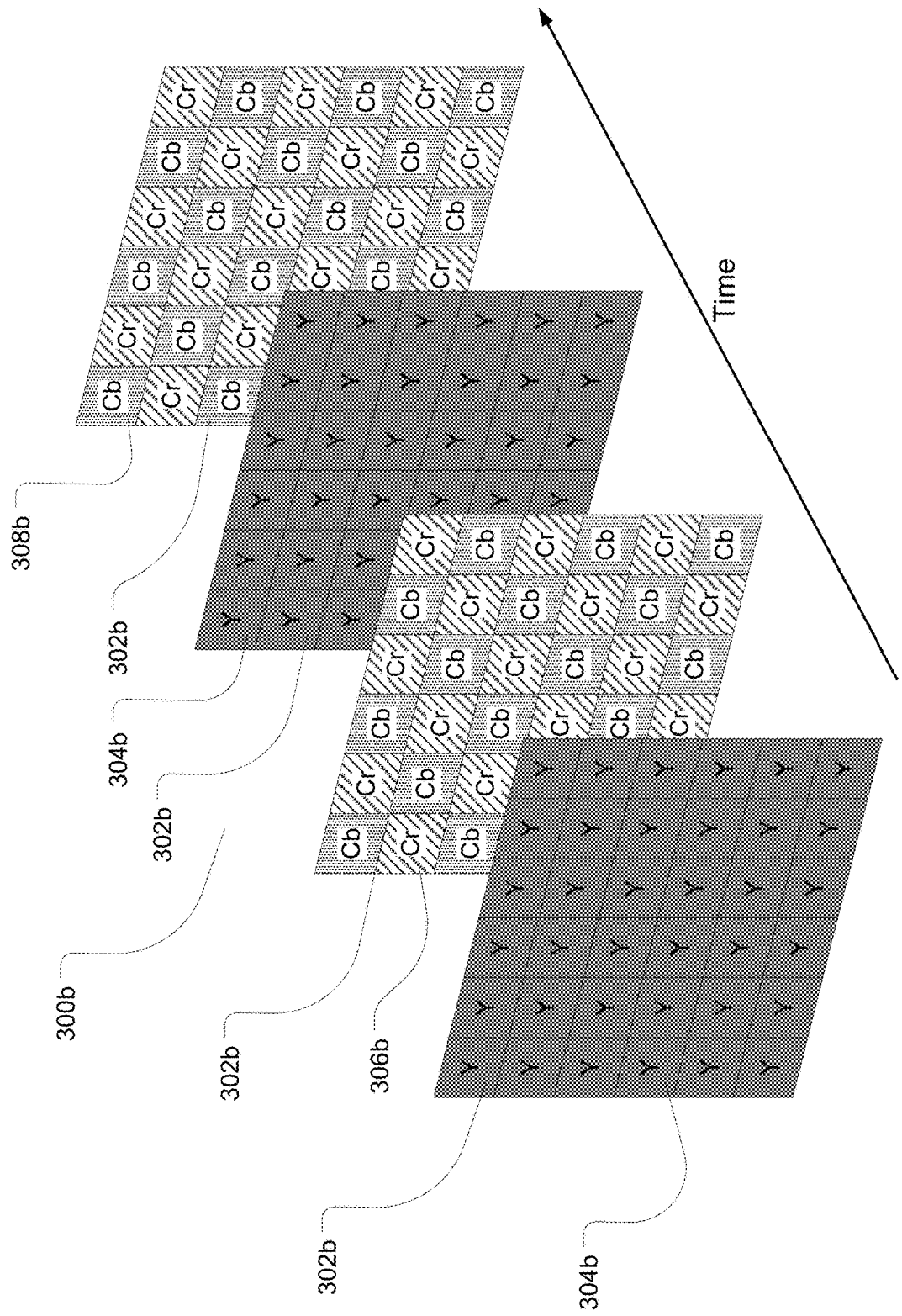
FIG. 3B illustrates a schematic of an embodiment of an operation sequence of chrominance and luminance frames in accordance with the principles and teachings of the disclosure.

In an embodiment, as illustrated in FIG. 3B, an endoscopic system 300b may comprise a pixel array 302b having uniform pixels and the system may be operated to receive Y (luminance pulse) 304b, λY+Cb (Modulated ChromaBlue) 306b and δY+Cr (Modulated ChromaRed) 308b pulses.

Figure 3C:
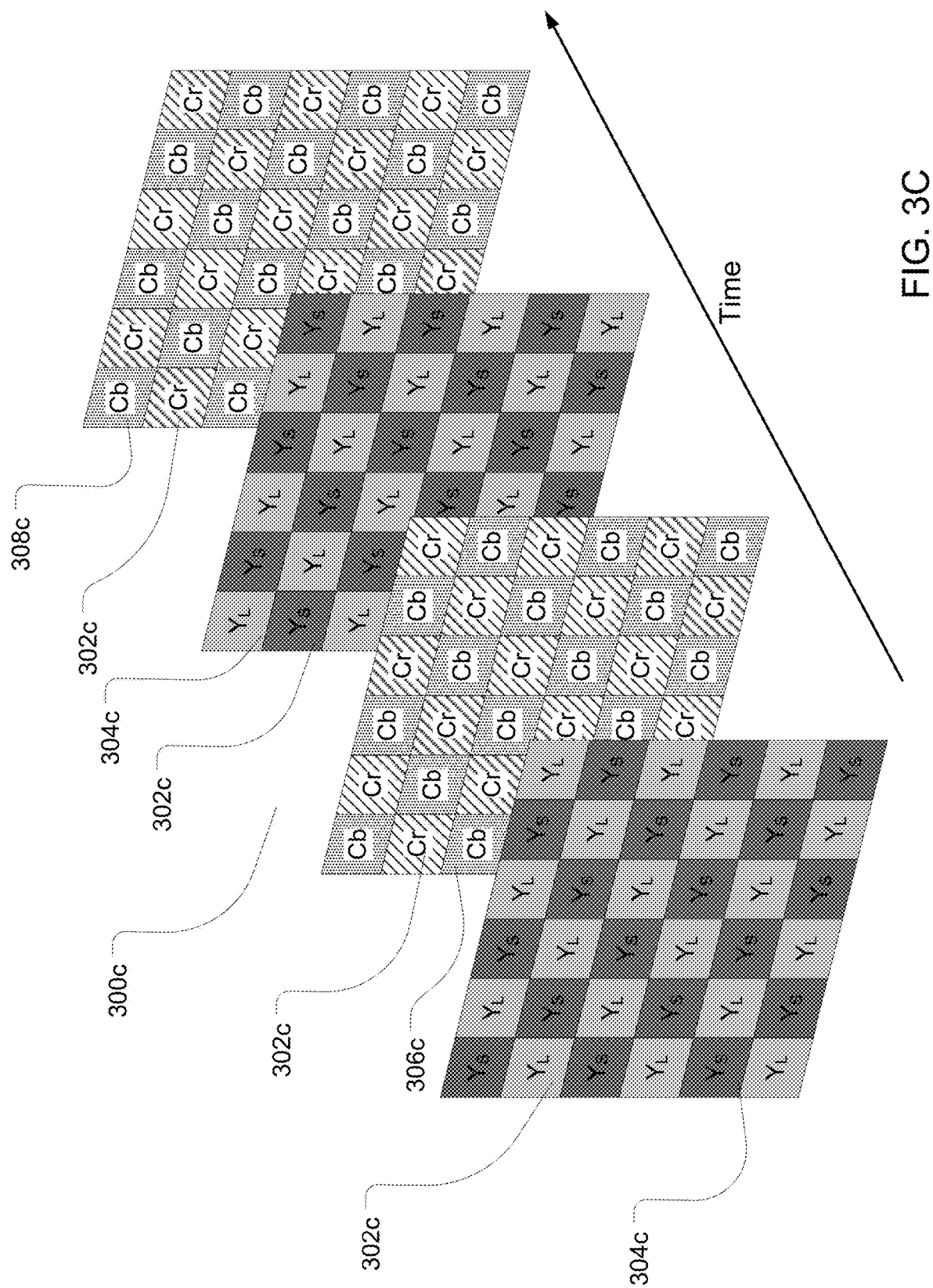
FIG. 3C illustrates a schematic of an embodiment of an operation sequence of chrominance and luminance frames in accordance with the principles and teachings of the disclosure.

In an embodiment, as illustrated in FIG. 3C, an endoscopic system 300c may comprise a pixel array 302c having checker patterned (alternating) pixels and the system may be operated to receive Y (luminance pulse) 304c, λY+Cb (Modulated ChromaBlue) 306c and δY+Cr (Modulated ChromaRed) 308c pulses. Within the luminance frames, the two exposure periods are applied for the purpose of extending the dynamic range (YL and YS, corresponding to the long and short exposures).

Figure 4:
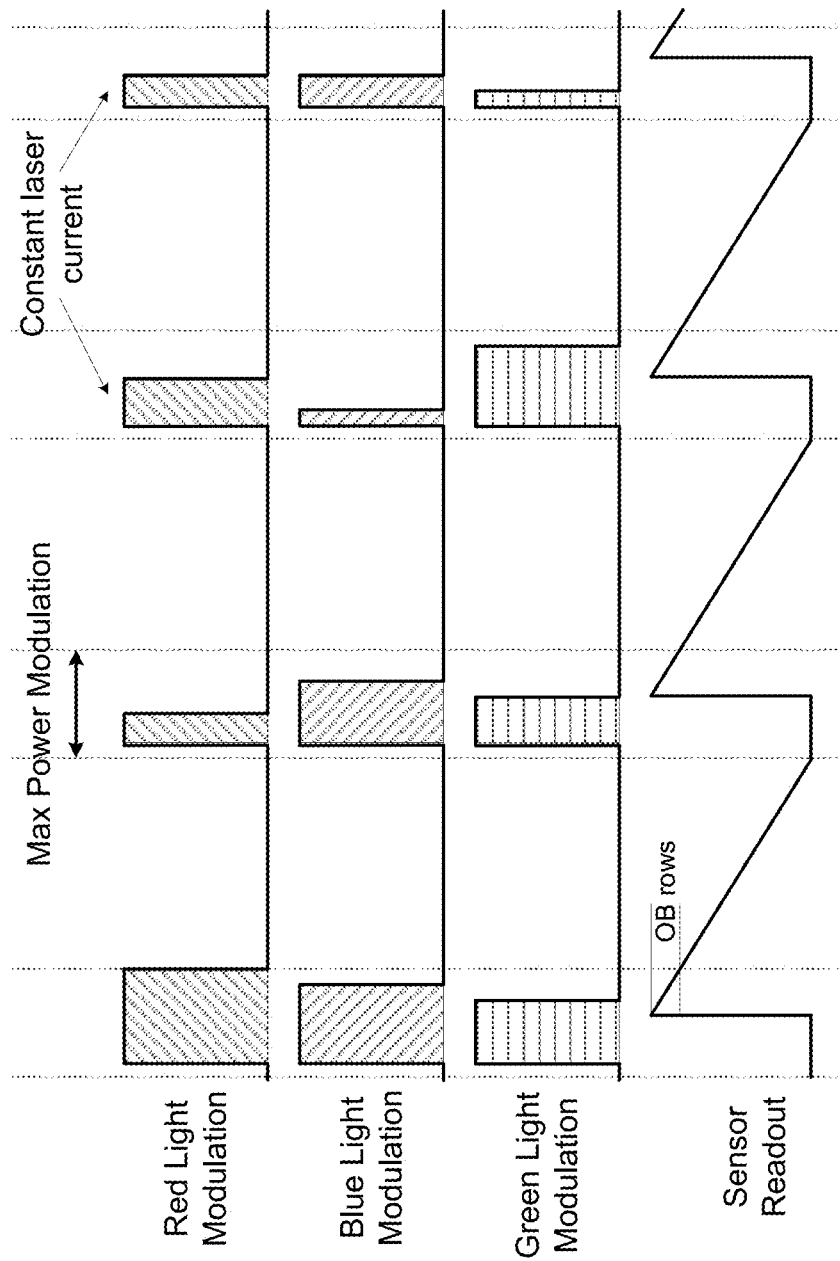
FIG. 4 illustrates an embodiment of sensor and emitter modulation in accordance with the principles and teachings of the disclosure.

FIG. 4 illustrates the general timing relationship within a 4-frame cycle, between pulsed mixtures of three wavelengths and the readout cycle of a monochrome CMOS sensor.

Figure 5:
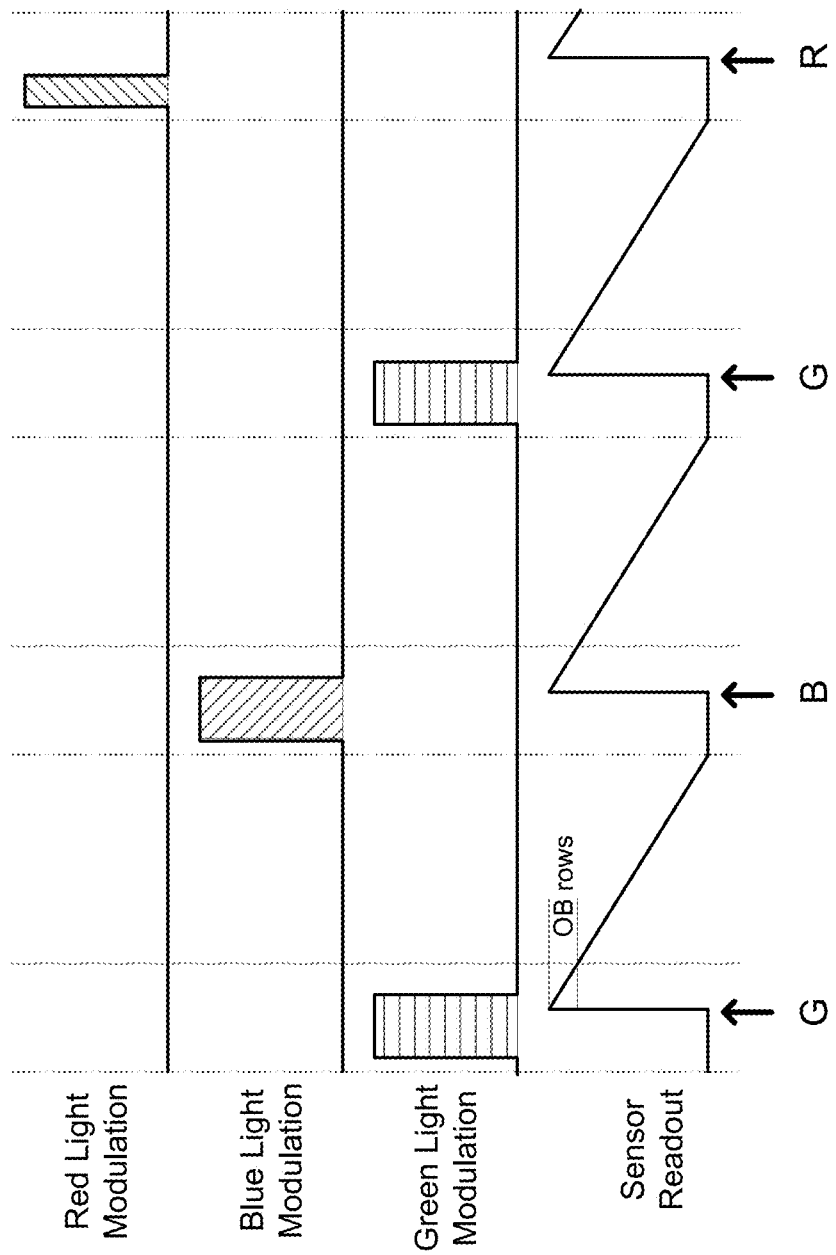
FIG. 5 illustrates an embodiment of sensor and emitter patterns in accordance with the principles and teachings of the disclosure.

Essentially there are three monochromatic pulsed light sources under the fast control of the camera and a special design of monochromatic CMOS image sensor which enables high final progressive video rates of 60 Hz or more. Periodic sequences of monochromatic red, green and blue frames are captured, e.g., with an R-G-B-G pattern, and assembled into sRGB images in the image signal processor chain (ISP). The light-pulse and sensor readout timing relationship is shown in FIG. 5. In order to provide pure luminance information in the same frame, all three sources are pulsed in unison with light energies that are modulated according to the color transformation coefficients that convert from RGB space to YCbCr (as per the ITU-R BT.709 HD standard):

$$\begin{bmatrix} Y \\ Cb \\ Cr \end{bmatrix} = \begin{bmatrix} R \\ G \\ B \end{bmatrix} \begin{bmatrix} 0.183 & 0.614 & 0.062 \\ -0.101 & -0.339 & 0.439 \\ 0.439 & -0.399 & -0.040 \end{bmatrix}$$

It will be appreciated that other color space conversion standards may be implemented by the disclosure, including but not limited to, ITU-R BT.709 HD standard, ITU-R BT.601 standard, and ITU-R BT.2020 standard.

If white balance is being performed in the illumination domain, then this modulation is imposed in addition to the white balance modulation.

To complete a full color image requires that the two components of chrominance also be provided. However, the same algorithm that was applied for luminance cannot be directly applied for chrominance images since it is signed, as reflected in the fact that some of the RGB coefficients are negative. The solution to this is to add a degree of luminance of sufficient magnitude that all of the final pulse energies become positive. As long as the color fusion process in the ISP is aware of the composition of the chrominance frames, they can be decoded by subtracting the appropriate amount of luminance from a neighboring frame. The pulse energy proportions are given by:

$$Y = 0.183 \cdot R + 0.614 \cdot G + 0.062 \cdot B$$
$$Cb = \lambda \cdot Y - 0.101 \cdot R - 0.339 \cdot G + 0.439 \cdot B$$
$$Cr = \delta \cdot Y + 0.439 \cdot R - 0.399 \cdot G - 0.040 \cdot B$$

where $$\lambda \geq \frac{0.339}{0.614} = 0.552$$

$$\delta \geq \frac{0.399}{0.614} = 0.650$$

Figure 6A:
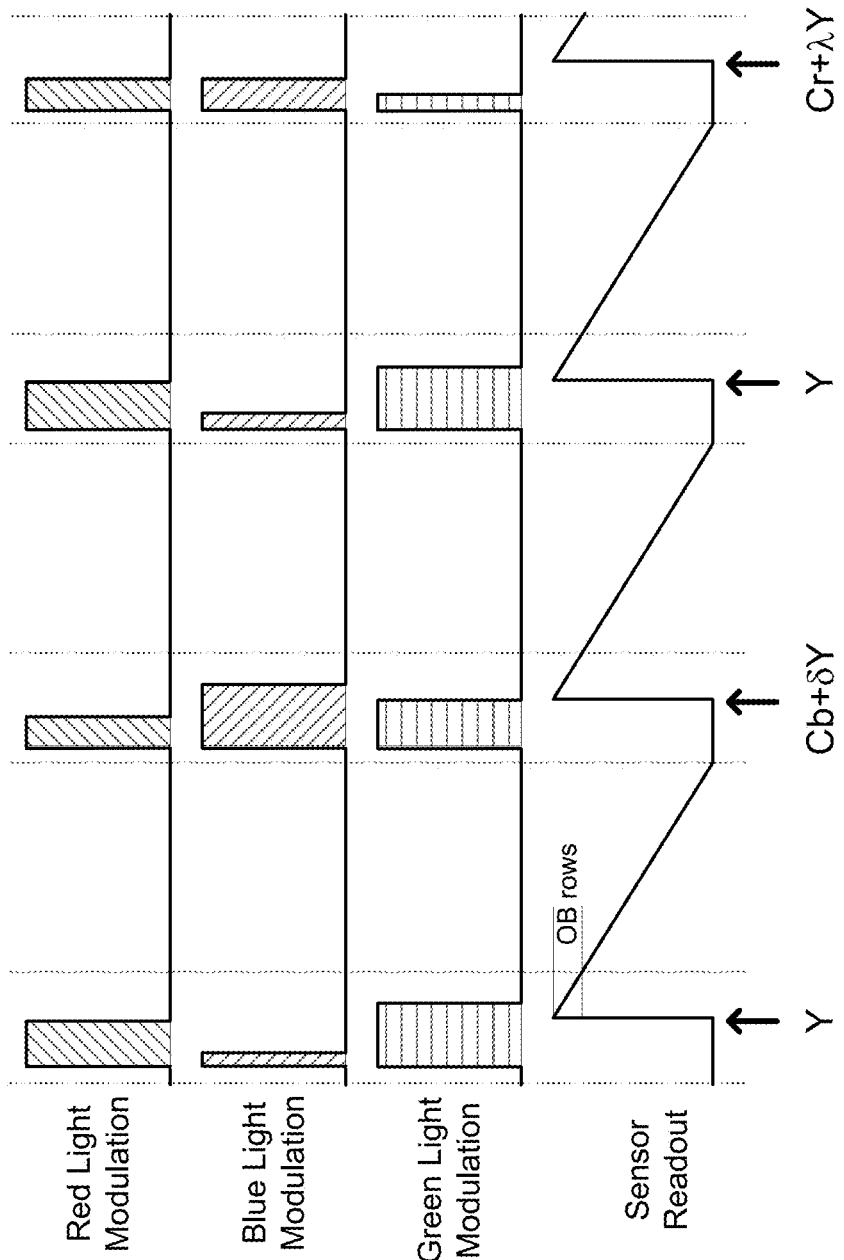
FIG. 6A illustrates an embodiment of sensor and emitter patterns in accordance with the principles and teachings of the disclosure.
Figure 6B:
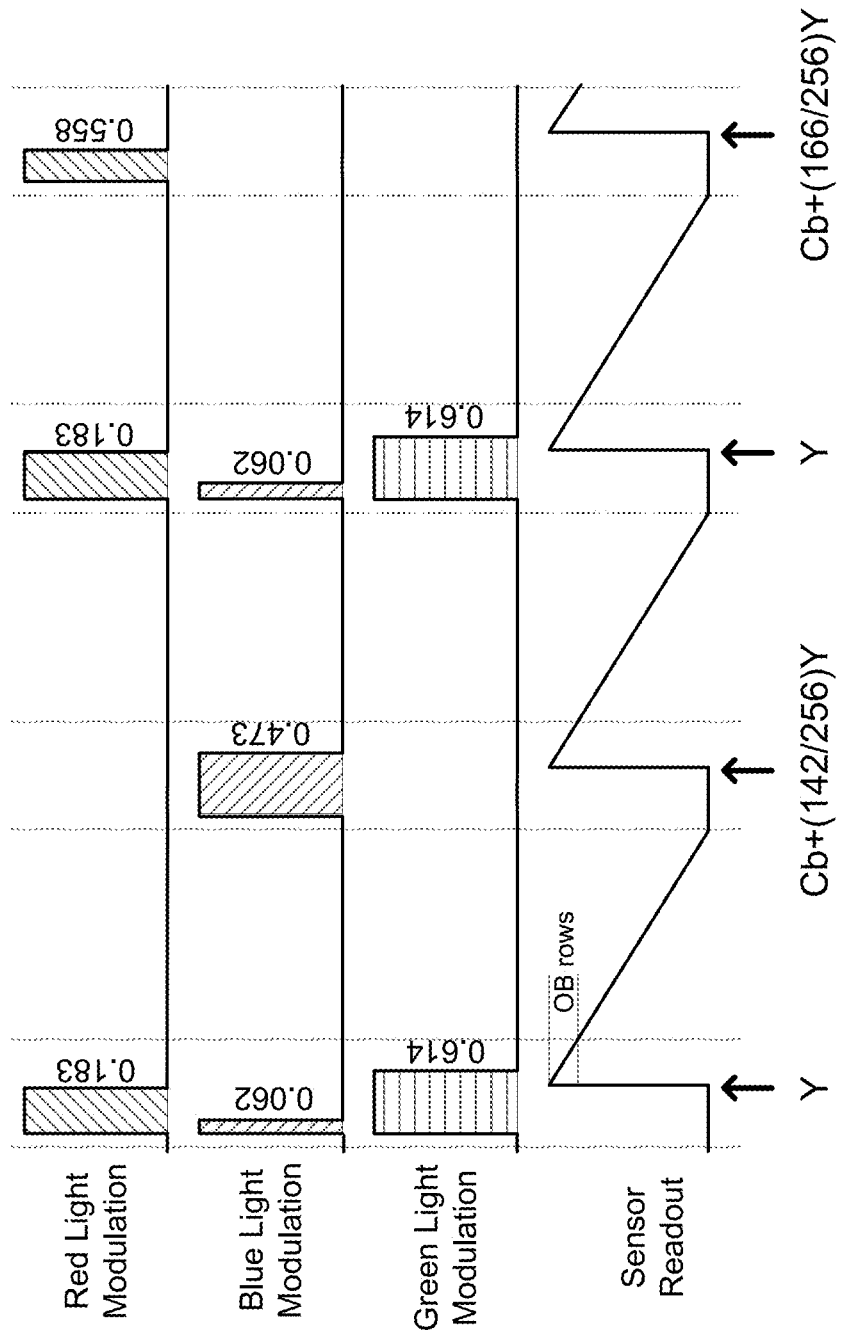
FIG. 6B illustrates an embodiment of sensor and emitter patterns in accordance with the principles and teachings of the disclosure.

The timing for the general case is shown in FIG. 6A. It turns out that if the λ factor is equal to 0.552; both the red and the green components are exactly cancelled, in which case the Cb information can be provided with pure blue light. Similarly, setting δ=0.650 cancels out the blue and green components for Cr which becomes pure red. This particular example is illustrated in FIG. 6B, which also depicts λ and δ as integer multiples of ½⁸. This is a convenient approximation for the digital frame reconstruction (see later discussion).

Figure 7:
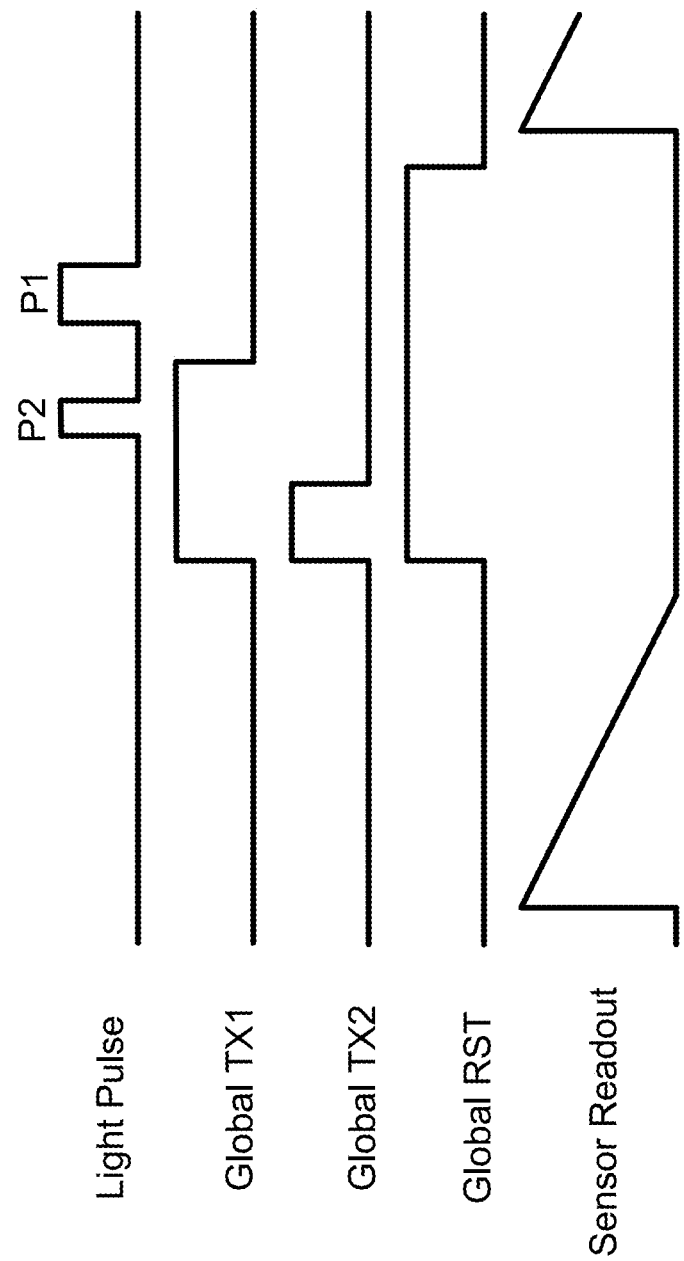
FIG. 7 illustrates a graphical representation of the operation of a pixel array having pixels of differing pixel sensitivities in accordance with the principles and teachings of the disclosure.

Referring now to FIG. 7, there is illustrated a general timing diagram for this process. The exposure periods for the two flavors of pixel are controlled by two internal signals within the image sensor, depicted as TX1 and TX2 in the figure. In fact, it is possible to do this at the same time as extending the dynamic range for the luminance frame, where it is most needed, since the two integration times can be adjusted on a frame by frame basis (see FIGS. 3a-3c). The benefit is that the color motion artifacts are less of an issue if all the data is derived from two frames versus three. There is of course a subsequent loss of spatial resolution for the chrominance data but that is of negligible consequence to the image quality for the reasons discussed earlier.

Figure 8:
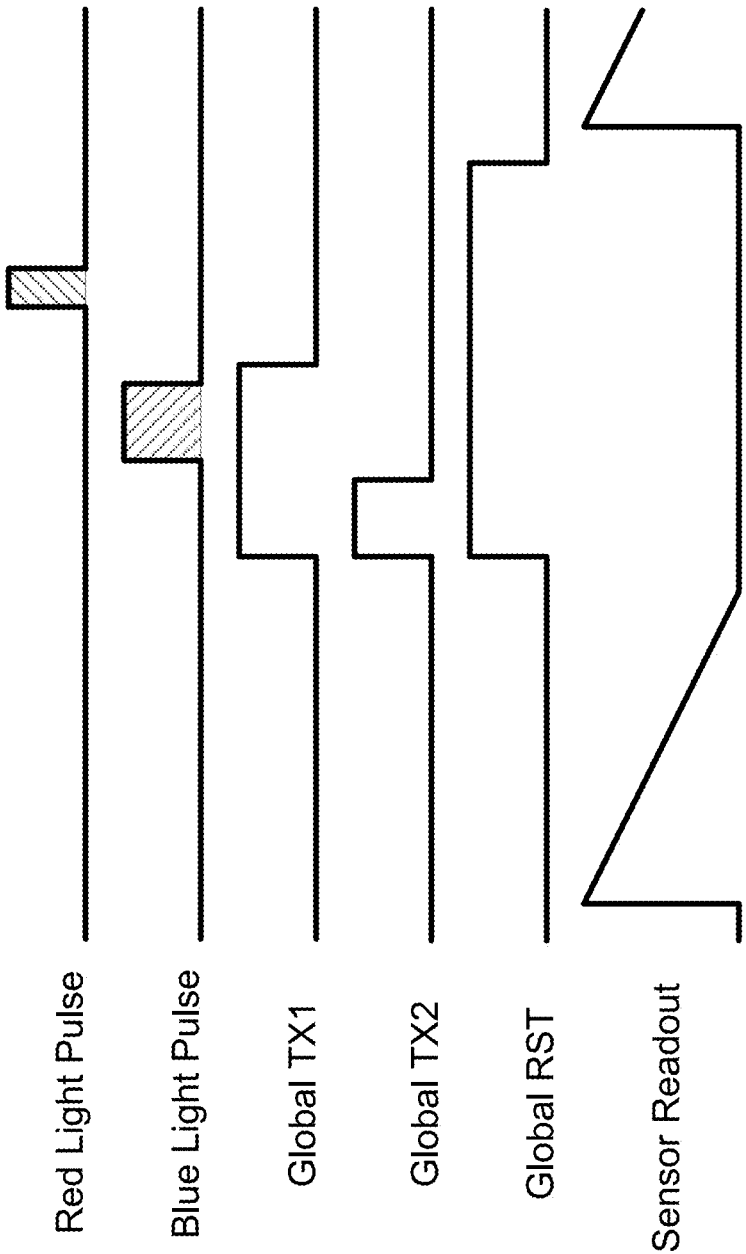
FIG. 8 illustrates a graphical representation of the operation of a pixel array having pixels of differing pixel sensitivities in accordance with the principles and teachings of the disclosure.

An inherent property of the monochrome wide dynamic range array is that the pixels that have the long integration time must integrate a superset of the light seen by the short integration time pixels. Co-pending U.S. patent application Ser. No. 13/952,564 entitled WIDE DYNAMIC RANGE USING MONOCHROMATIC SENSOR is hereby incorporated by this reference into this disclosure as if fully set forth herein. For regular wide dynamic range operation in the luminance frames, that is desirable. For the chrominance frames it means that the pulsing must be controlled in conjunction with the exposure periods so as to provide, e.g., λY+Cb from the start of the long exposure and switch to δY+Cr at the point that the short pixels are turned on (both pixel types have their charges transferred at the same time). During color fusion, this would be accounted for. FIG. 8 shows the specific timing diagram for this solution.

A typical ISP involves first taking care of any necessary sensor and optical corrections (such as defective pixel elimination, lens shading etc.), then in turn; white balance, demosaic/color fusion and color correction.

Figure 9:
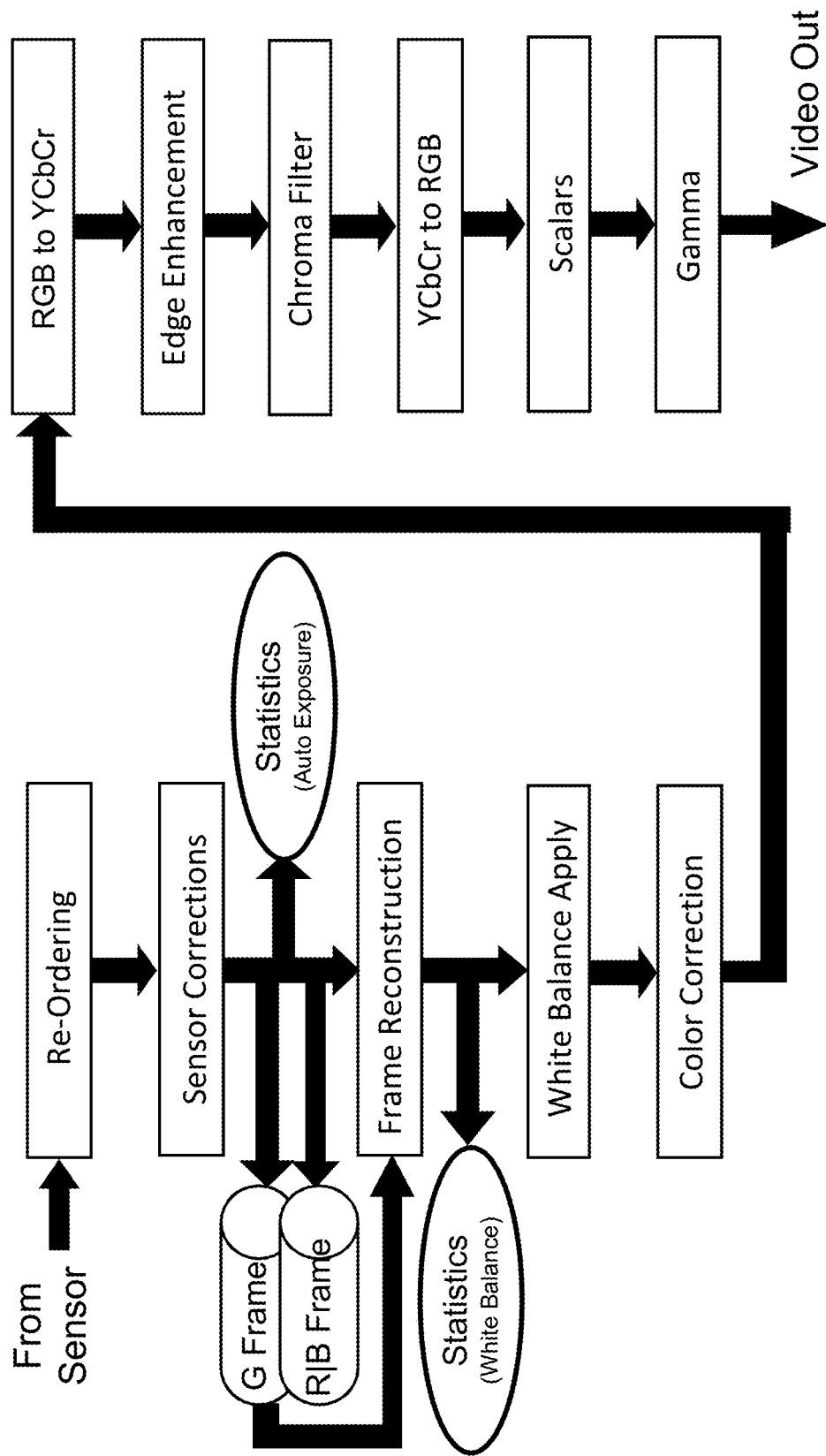
FIG. 9 illustrates a flow chart of the operation of a pixel array in accordance with the principles and teachings of the disclosure.

Before finally applying gamma to place the data in the standard sRGB space, there might typically be some operations (e.g., edge enhancement) and/or adjustments (e.g., saturation) performed in an alternative color space such as YCbCr or HSL. FIG. 9 depicts a basic ISP core that would be appropriate for the R-G-B-G pulsing scheme. In this example, the data is converted to YCbCr in order to apply edge enhancement in the luminance plane and conduct filtering of the chrominance, then converted back to linear RGB.

Figure 10:
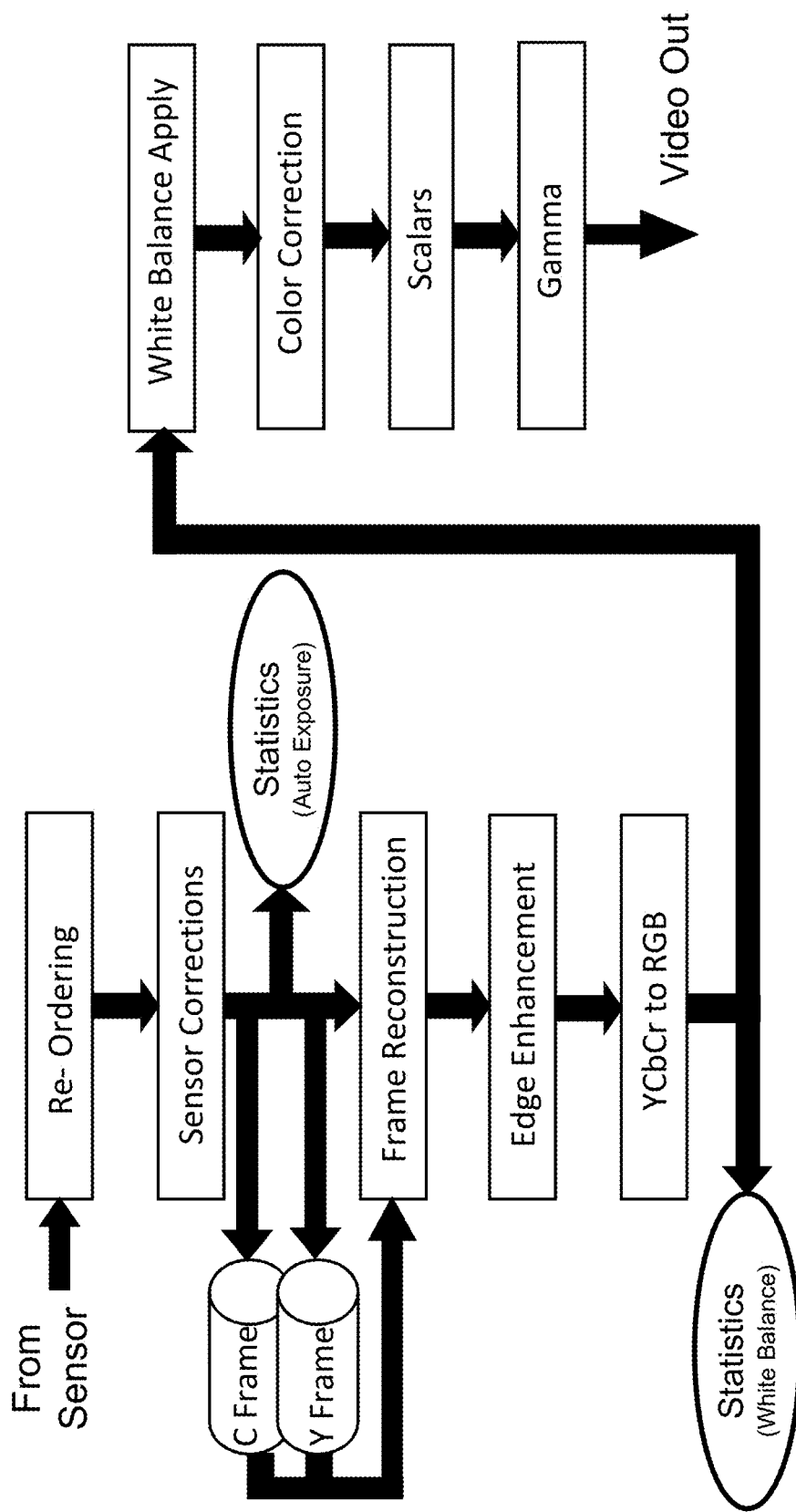
FIG. 10 illustrates a flow chart of the operation of a pixel array in accordance with the principles and teachings of the disclosure.

In the case of the Y-Cb-Y-Cr pulsing scheme, the image data is already in the YCbCr space following the color fusion. Therefore, in this case it makes sense to perform luminance and chrominance based operations up front, before converting back to linear RGB to perform the color correction etc. See FIG. 10.

Figure 11:
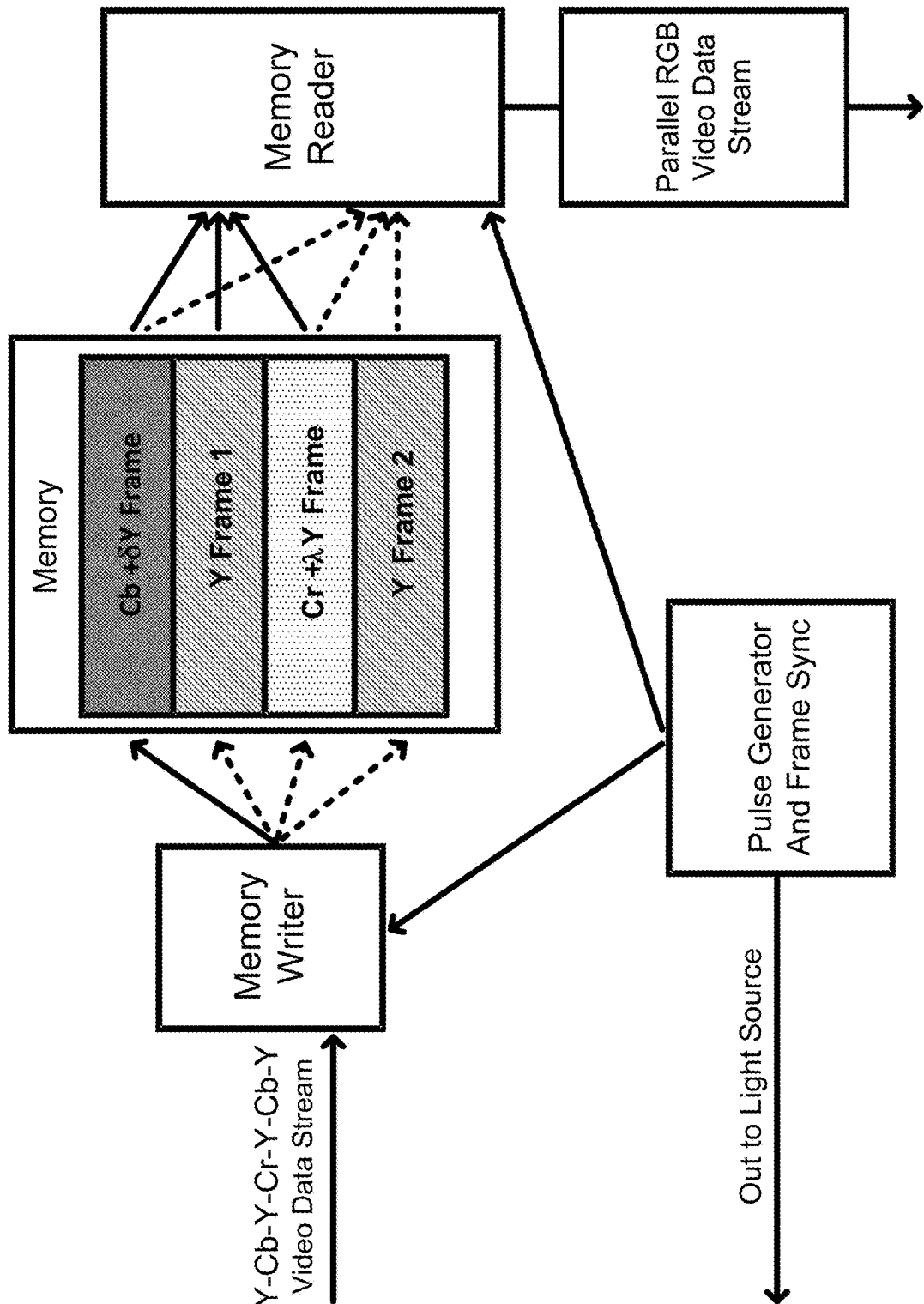
FIG. 11 illustrates a flow chart of the operation of a pixel array in accordance with the principles and teachings of the disclosure.

The color fusion process is more straightforward than de-mosaic, which is necessitated by the Bayer pattern, since there is no spatial interpolation. It does require buffering of frames though in order to have all of the necessary information available for each pixel, as indicated in FIG. 11. FIG. 12A shows the general situation of pipelining of data for the Y-Cb-Y-Cr pattern which yields 1 full color image per two raw captured images. This is accomplished by using each chrominance sample twice. In FIG. 12B the specific example of a 120 Hz frame capture rate providing 60 Hz final video is drawn.

The linear Y, Cb and Cr components for each pixel may be computed thus:

$$Y_i = 2^{m-4} + (x_{i,n-1} - K)$$

$$\left\{\begin{array}{l} Cb_i = 2^{m-1} + (x_{i,n} - K) - \lambda \cdot (x_{i,n-1} - K) \\ Cr_i = 2^{m-1} + (x_{i,n-2} - K) - \delta \cdot (x_{i,n-1} - K) \end{array}\right\} \text{ when } n = \text{'}Cb\text{' frame}$$

$$\left\{\begin{array}{l} Cb_i = 2^{m-1} + (x_{i,n-2} - K) - \lambda \cdot (x_{i,n-1} - K) \\ Cr_i = 2^{m-1} + (x_{i,n} - K) - \delta \cdot (x_{i,n-1} - K) \end{array}\right\} \text{ when } n = \text{'}Cr\text{' frame}$$

Where $x_{i,n}$ is the input data for pixel i in frame n, m is the pipeline bit-width of the ISP and K is the ISP black offset level at the input to the color fusion block, (if applicable). Since chrominance is signed it is conventionally centered at 50% of the digital dynamic range ($2^{m-1}$).

If two exposures are used to provide both chrominance components in the same frame as described earlier, the two flavors of pixel are separated into two buffers. The empty pixels are then filled in using, e.g., linear interpolation. At this point, one buffer contains a full image of δY+Cr data and the other; δY+Cr+λY+Cb. The δY+Cr buffer is subtracted from the second buffer to give λY+Cb. Then the appropriate proportion of luminance data from the Y frames is subtracted out for each.

Implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked in order to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Figure 13:
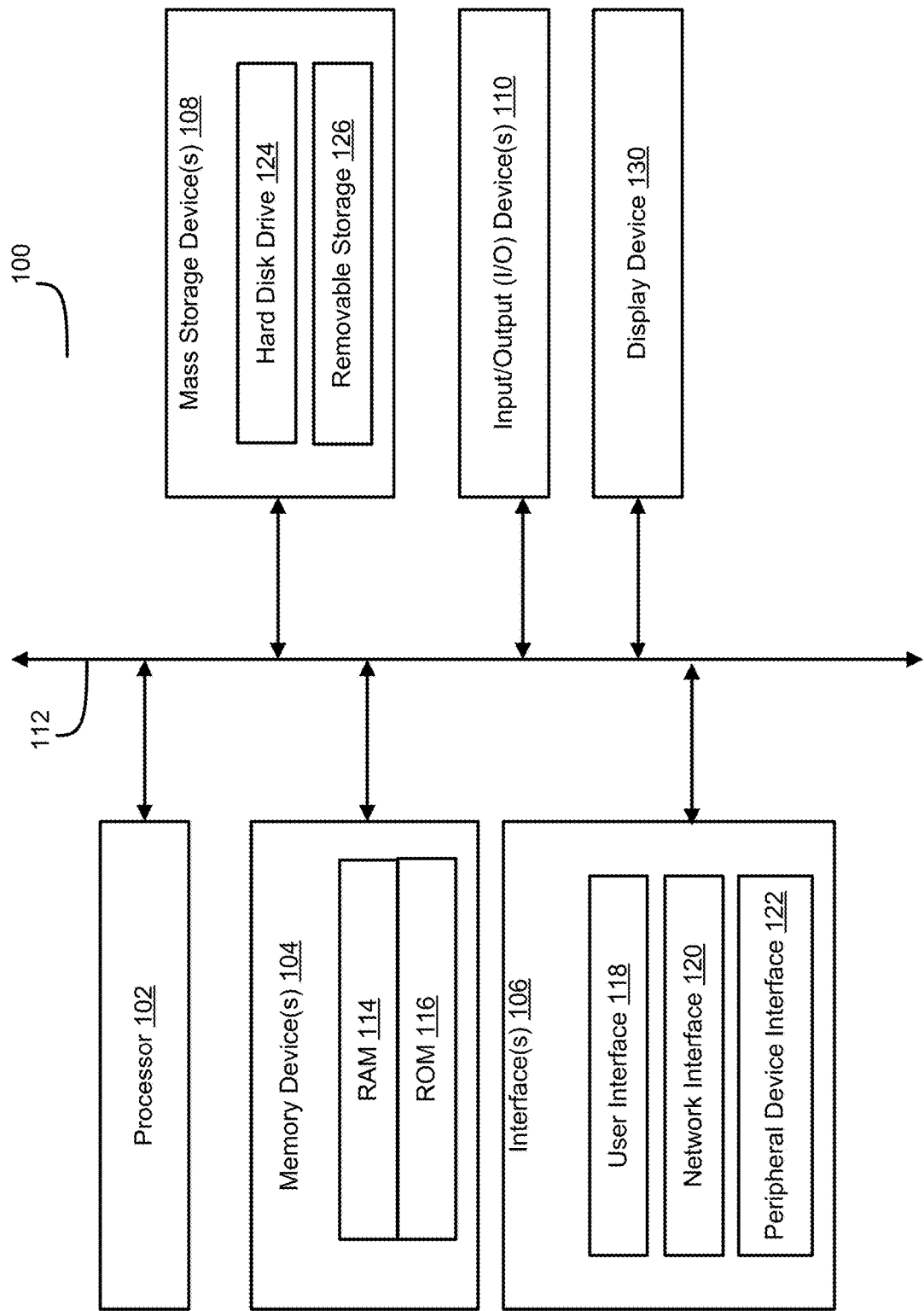
FIG. 13 illustrates an embodiment of supporting hardware in accordance with the principles and teachings of the disclosure.

As can be seen in FIG. 13, various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined herein is not necessarily limited to the described features or acts described above. Rather, the described features and acts are disclosed as examples.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms are used throughout the following description to refer to particular system components. As one skilled in the art will appreciate, components may be referred to by different names. This document does not intend to distinguish between components that differ in name, but not function.

FIG. 13 is a block diagram illustrating an example computing device 100. Computing device 100 may be used to perform various procedures, such as those discussed herein. Computing device 100 can function as a server, a client, or any other computing entity. Computing device can perform various monitoring functions as discussed herein, and can execute one or more application programs, such as the application programs described herein. Computing device 100 can be any of a wide variety of computing devices, such as a desktop computer, a notebook computer, a server computer, a handheld computer, camera control unit, tablet computer and the like.

Computing device 100 includes one or more processor(s) 102, one or more memory device(s) 104, one or more interface(s) 106, one or more mass storage device(s) 108, one or more Input/Output (I/O) device(s) 110, and a display device 130 all of which are coupled to a bus 112. Processor(s) 102 include one or more processors or controllers that execute instructions stored in memory device(s) 104 and/or mass storage device(s) 108. Processor(s) 102 may also include various types of computer-readable media, such as cache memory.

Memory device(s) 104 include various computer-readable media, such as volatile memory (e.g., random access memory (RAM) 114) and/or nonvolatile memory (e.g., read-only memory (ROM) 116). Memory device(s) 104 may also include rewritable ROM, such as Flash memory.

Mass storage device(s) 108 include various computer readable media, such as magnetic tapes, magnetic disks, optical disks, solid-state memory (e.g., Flash memory), and so forth. As shown in FIG. 13, a particular mass storage device is a hard disk drive 124. Various drives may also be included in mass storage device(s) 108 to enable reading from and/or writing to the various computer readable media. Mass storage device(s) 108 include removable media 126 and/or non-removable media.

I/O device(s) 110 include various devices that allow data and/or other information to be input to or retrieved from computing device 100. Example I/O device(s) 110 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 130 includes any type of device capable of displaying information to one or more users of computing device 100. Examples of display device 130 include a monitor, display terminal, video projection device, and the like.

Interface(s) 106 include various interfaces that allow computing device 100 to interact with other systems, devices, or computing environments. Example interface(s) 106 may include any number of different network interfaces 120, such as interfaces to local area networks (LANs), wide area networks (WANs), wireless networks, and the Internet. Other interface(s) include user interface 118 and peripheral device interface 122. The interface(s) 106 may also include one or more user interface elements 118. The interface(s) 106 may also include one or more peripheral interfaces such as interfaces for printers, pointing devices (mice, track pad, etc.), keyboards, and the like.

Bus 112 allows processor(s) 102, memory device(s) 104, interface(s) 106, mass storage device(s) 108, and I/O device(s) 110 to communicate with one another, as well as other devices or components coupled to bus 112. Bus 112 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 100, and are executed by processor(s) 102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Figure 14A:
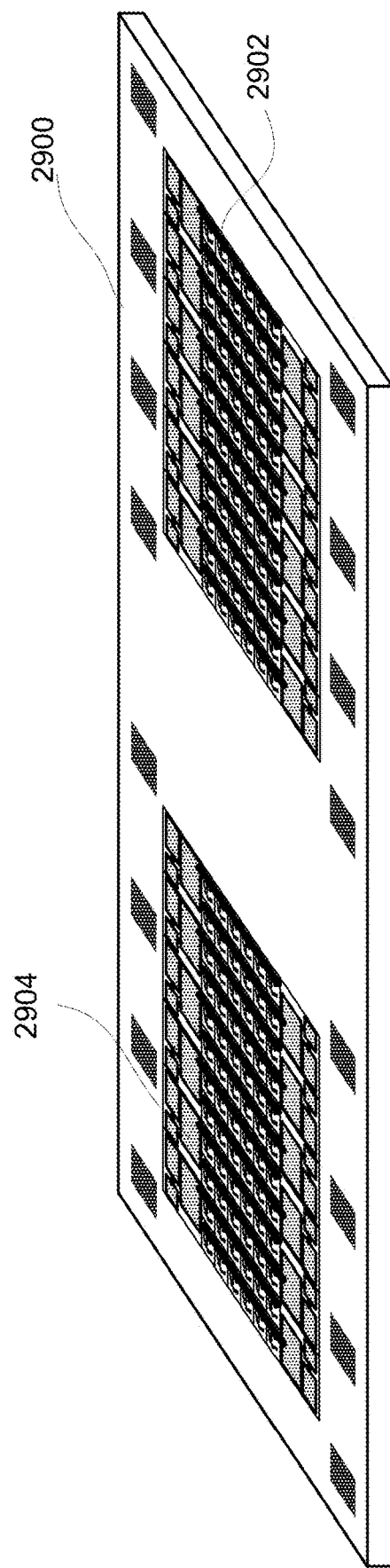
FIGS. 14A and 14B illustrate an implementation having a plurality of pixel arrays for producing a three dimensional image in accordance with the teachings and principles of the disclosure.
Figure 14B:
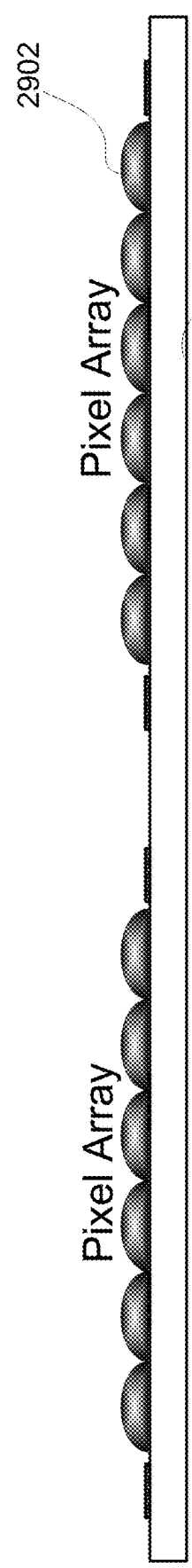

FIGS. 14A and 14B illustrate a perspective view and a side view, respectively, of an implementation of a monolithic sensor 2900 having a plurality of pixel arrays for producing a three dimensional image in accordance with the teachings and principles of the disclosure. Such an implementation may be desirable for three dimensional image capture, wherein the two pixel arrays 2902 and 2904 may be offset during use. In another implementation, a first pixel array 2902 and a second pixel array 2904 may be dedicated to receiving a predetermined range of wave lengths of electromagnetic radiation, wherein the first pixel array is dedicated to a different range of wave length electromagnetic radiation than the second pixel array.

Figure 15A:
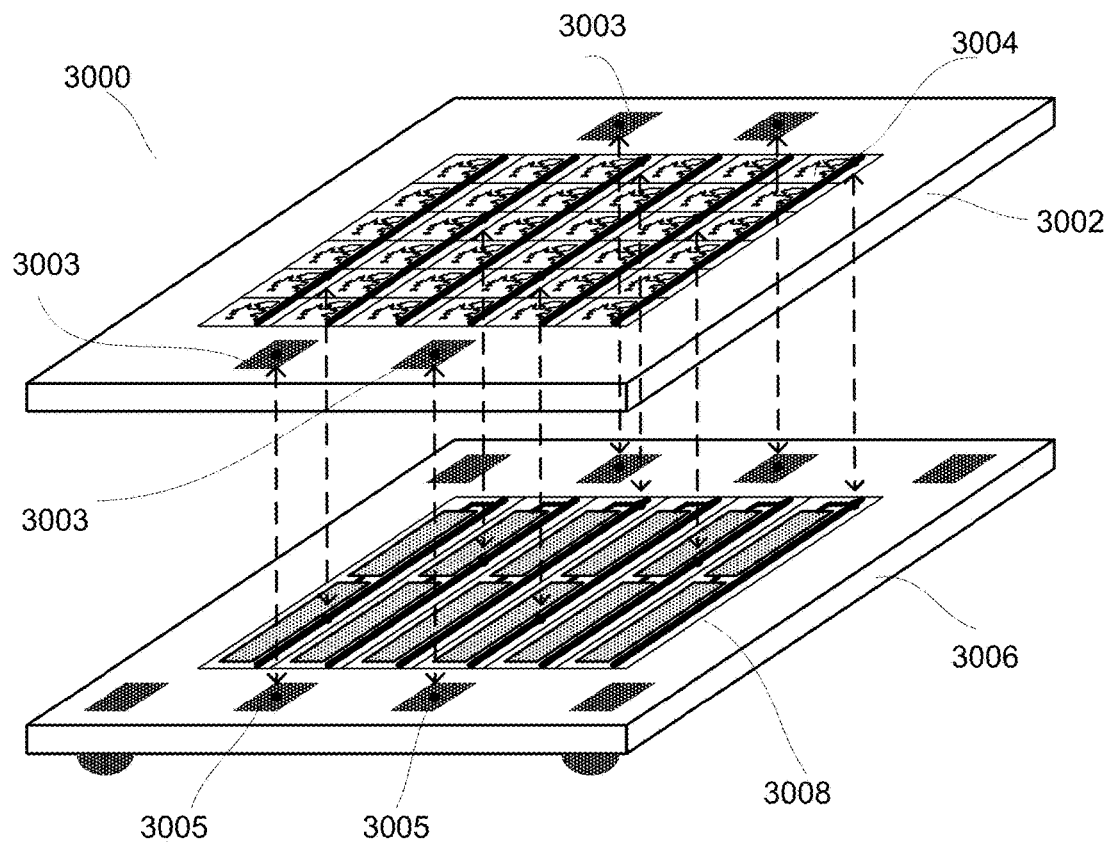
FIGS. 15A and 15B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 15B:
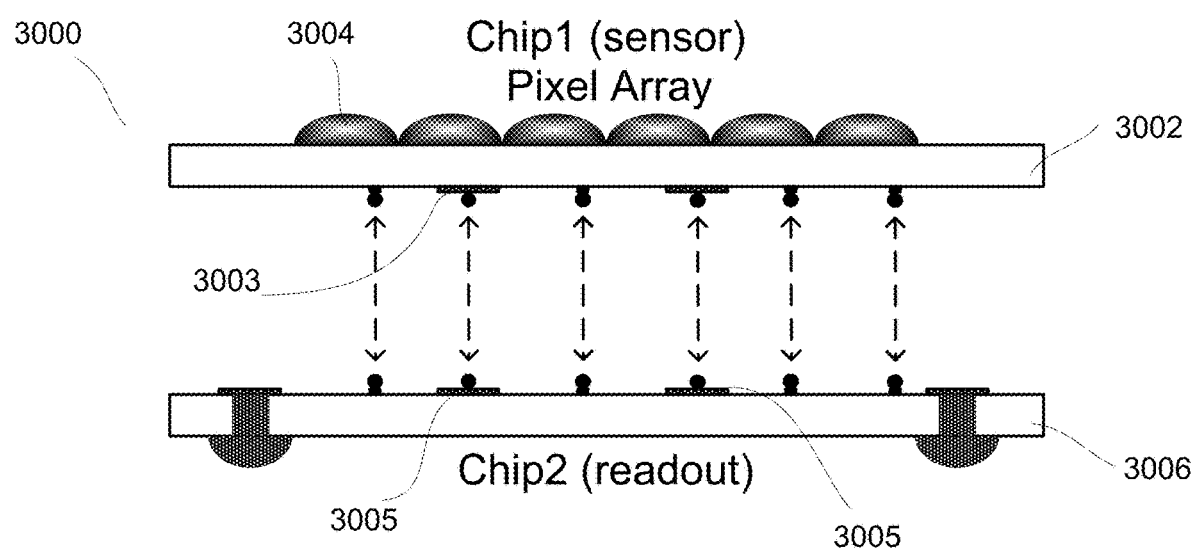

FIGS. 15A and 15B illustrate a perspective view and a side view, respectively, of an implementation of an imaging sensor 3000 built on a plurality of substrates. As illustrated, a plurality of pixel columns 3004 forming the pixel array are located on the first substrate 3002 and a plurality of circuit columns 3008 are located on a second substrate 3006. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 3002 of the two substrates/chips may be processed using an image CMOS process. The first substrate/chip 3002 may be comprised either of a pixel array exclusively or a pixel array surrounded by limited circuitry. The second or subsequent substrate/chip 3006 may be processed using any process, and does not have to be from an image CMOS process. The second substrate/chip 3006 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 3002 may be stacked with the second or subsequent substrate/chip 3006 using any three-dimensional technique. The second substrate/chip 3006 may support most, or a majority, of the circuitry that would have otherwise been implemented in the first image CMOS chip 3002 (if implemented on a monolithic substrate/chip) as peripheral circuits and therefore have increased the overall system area while keeping the pixel array size constant and optimized to the fullest extent possible. The electrical connection between the two substrates/chips may be done through interconnects 3003 and 3005, which may be wirebonds, bump and/or TSV (Through Silicon Via).

Figure 16A:
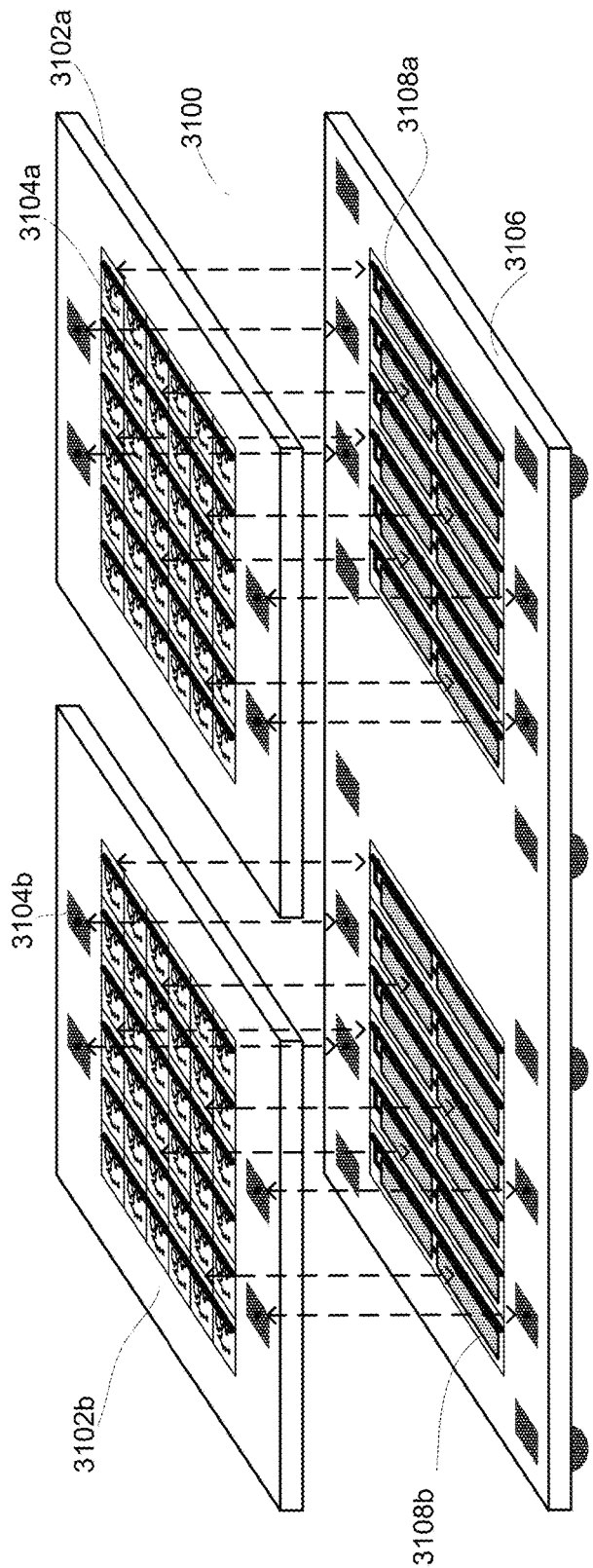
FIGS. 16A and 16B illustrate a perspective view and a side view, respectively, of an implementation of an imaging sensor having a plurality of pixel arrays for producing a three dimensional image, wherein the plurality of pixel arrays and the image sensor are built on a plurality of substrates.
Figure 16B:
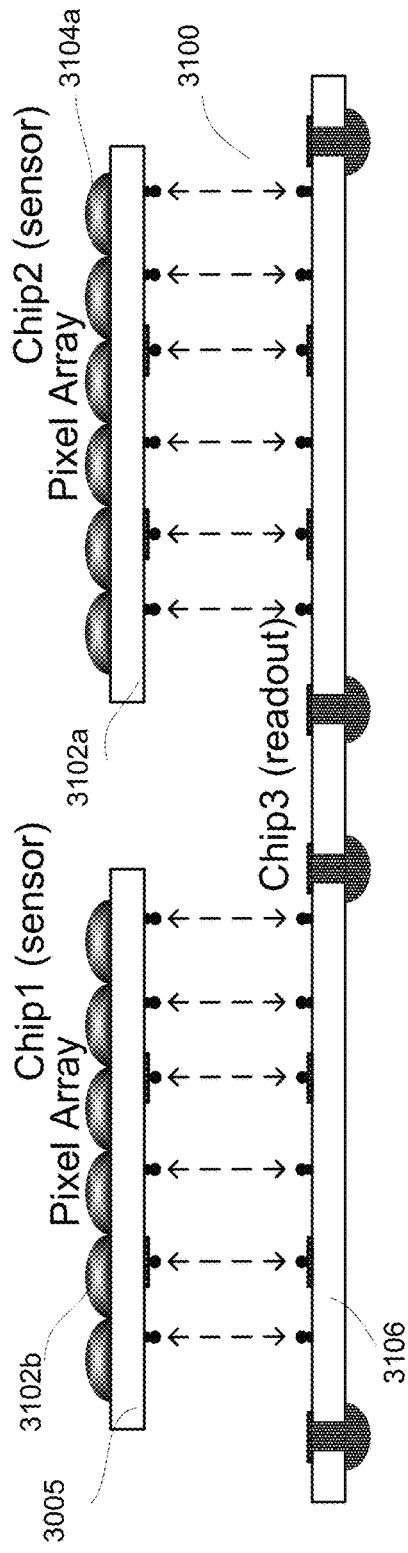

FIGS. 16A and 16B illustrate a perspective view and a side view, respectively, of an implementation of an imaging sensor 3100 having a plurality of pixel arrays for producing a three dimensional image. The three dimensional image sensor may be built on a plurality of substrates and may comprise the plurality of pixel arrays and other associated circuitry, wherein a plurality of pixel columns 3104a forming the first pixel array and a plurality of pixel columns 3104b forming a second pixel array are located on respective substrates 3102a and 3102b, respectively, and a plurality of circuit columns 3108a and 3108b are located on a separate substrate 3106. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

In an embodiment, a method for digital imaging for use with an endoscope in ambient light deficient environments may comprise: actuating an emitter to emit a plurality of pulses of electromagnetic radiation to cause illumination within the light deficient environment, wherein said pulses comprise a first pulse that is within a first wavelength range that comprises a first portion of electromagnetic spectrum, wherein said pulses comprise a second pulse that is within a second wavelength range that comprises a second portion of electromagnetic spectrum, wherein said pulses comprise a third pulse that is with is a third wavelength range that comprises a third portion of electromagnetic spectrum; pulsing said plurality of pulses at a predetermined interval; sensing reflected electromagnetic radiation from said pulses with a pixel array to create a plurality of image frames, wherein said pixel array is read at an interval that corresponds to the pulse interval of said laser emitter; and creating a stream of images by combining the plurality of image frames to form a video stream. In an embodiment, said first pulse comprises chrominance red. In an embodiment, said second pulse comprises chrominance blue. In an embodiment, said third pulse comprises a luminance pulse. In an embodiment, said luminance pulse is created by pulsing a red pulse and a blue pulse and a green pulse. In such an embodiment, said red pulse is modulated relative to the blue and green pulse such that the red pulse has a positive chrominance value. In an embodiment, said blue pulse is modulated relative to the red and green pulse such that the blue pulse has a positive chrominance value. In an embodiment, said green pulse is modulated relative to the blue and red pulse such that the green pulse has a positive chrominance value. In an embodiment, the method further comprises modulating the plurality of pulses by a value such that the chrominance value of each pulse is positive. In an embodiment, the method further comprises removing pulse modulation values from during image stream construction. In such an embodiment, the process of modulating comprises adding a luminance value to the plurality of pulses. In an embodiment, the luminance value for modulation is an integer that is a multiple of $(½)^8$. In an embodiment, a luminance value for modulation of 0.552 cancels out red chrominance and green chrominance. In an embodiment, a luminance value for modulation of 0.650 cancels out blue chrominance and green chrominance. In an embodiment, the method further comprises reducing noise while creating the stream of image frames. In an embodiment, the method further comprises adjusting white balance while creating the stream of mage frames. In an embodiment, said third pulse is a luminance pulse that is pulses twice as often as the first and second pulses. In an embodiment, said luminance pulse is sensed by long exposure pixel and short exposure pixels within a pixel array. In an embodiment, the method further comprises sensing data generated by a plurality of pixel arrays and combining said data into a three dimensional image stream.

It will be appreciated that various features disclosed herein provide significant advantages and advancements in the art. The following embodiments are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the disclosure requires more features than are expressly recited in each claim, if any. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description to refer to particular system components. As one skilled in the art will appreciate, components may be referred to by different names. This document does not intend to distinguish between components that differ in name, but not function.

What is claimed is:

1. A system for digital imaging in an ambient light deficient environment comprising:
   an emitter configured to emit a plurality of pulses of electromagnetic radiation;
   an imaging sensor comprising an array of pixels for sensing electromagnetic radiation; and a control unit comprising a processor and wherein the control unit is in electrical communication with the imaging sensor and the emitter;

wherein the control unit is configured to synchronize the emitter and the imaging sensor to produce a plurality of image reference frames;

wherein the imaging sensor generates image data from sensed electromagnetic radiation that produces the plurality of image reference frames comprising:
- a first luminance frame comprising first luminance image data;
- a second luminance frame comprising second luminance image data;
- a first chrominance frame comprising first chrominance data;
- a second chrominance frame comprising second chrominance data; and
- a third chrominance frame comprising third chrominance data;

wherein the first luminance frame, the first chrominance frame, and the second chrominance frame are combined to form a first color image frame;

wherein the second chrominance frame is reused such that the second chrominance frame is combined with the third chrominance frame and the second luminance frame to form a second color image frame.

2. The system of claim 1, wherein the plurality of image reference frames comprises a plurality of chrominance frames and a plurality of luminance frames; and
   wherein the plurality of chrominance frames in the plurality of image reference frames alternate between blue chrominance frames having blue chrominance data and red chrominance frames having red chrominance data.

3. The system of claim 1, wherein the first chrominance frame has blue chrominance data, the second chrominance frame has red chrominance data, and the third chrominance frame has blue chrominance data; or
   wherein the first chrominance frame has red chrominance data, wherein the second chrominance frame has blue chrominance data, and the third chrominance frame has red chrominance data.

4. The system of claim 1, wherein the plurality of image reference frames further comprises:
   a third luminance frame comprising third luminance image data; and
   a fourth chrominance frame comprising fourth chrominance data;
   wherein the third chrominance frame is combined with the fourth chrominance frame and a third luminance frame to form a third color image frame.

5. The system of claim 4, wherein the first chrominance frame has blue chrominance data, the second chrominance frame has red chrominance data, the third chrominance frame has blue chrominance data, and the fourth chrominance frame has red chrominance data; or
   wherein the first chrominance frame has red chrominance data, the second chrominance frame has blue chrominance data, the third chrominance frame has red chrominance data, and the fourth chrominance frame has blue chrominance data.

6. The system of claim 2, wherein luminance frames are represented in the plurality of image reference frames twice as often as red chrominance frames and twice as often as blue chrominance frames.

7. The system of claim 2, wherein each of the plurality of chrominance frames in the plurality of images is used in at least two color image frames.

8. The system of claim 1, wherein the plurality of image reference frames produced by the imaging sensor comprises:
   a luminance frame of long exposure pixel data and short exposure pixel data;
   a red chrominance frame of long exposure pixel data and short exposure pixel data; and
   a blue chrominance frame of long exposure pixel data and short exposure pixel data.

9. The system of claim 1, wherein the emitter produces a pulsing pattern of luminance, chrominance blue, luminance, chrominance red.

10. The system of claim 1, wherein the emitter produces a pulsing pattern of luminance, chrominance blue combined with chrominance red, luminance, chrominance blue combined with chrominance red.

11. The system of claim 1, wherein the emitter comprises a plurality of sources that each emit a pulse of a portion of electromagnetic spectrum.

12. The system of claim 11, wherein the plurality of sources are configured to be actuated simultaneously and wherein the plurality of sources are configured to produce a pulse of a predetermined interval.

13. The system of claim 12, wherein the pulse of the predetermined interval is adjusted to provide luminance information during generation of luminance frames by matching to color space conversion coefficients.

14. The system of claim 12, wherein the pulse of the predetermined interval is adjusted to provide chrominance information during generation of chrominance frames by matching to color space conversion coefficients.

15. The system of claim 1, wherein a luminance coefficient is added to chrominance frames by an image signal processor and wherein the luminance coefficient is an integer that is a multiple of $(½)^n$.

16. The system of claim 1, wherein the imaging sensor is a monochrome sensor.

17. The system of claim 1, wherein the plurality of electromagnetic wavelengths are emitted at differing magnitudes, wherein the differing magnitudes correspond to the imaging sensor's sensitivity to differing wavelengths.

18. The system of claim 1, wherein the system further comprises an endoscope for accessing the ambient light deficient environment comprising a lumen and a hand piece;
   wherein the imaging sensor is disposed within one of the lumen and the hand piece.

19. The system of claim 1, wherein the system produces one color image frame per two captured image reference frames of the plurality of image reference frames.

20. The system of claim 19, wherein the emitter is pulsed and the plurality of image reference frames are captured at a rate of 120 Hz; and
   wherein the plurality of image reference frames are combined to produce a plurality of color image frames;
   wherein the plurality of color image frames are combined into a video stream having a frame rate of 60 Hz.

* * * * *